(12) United States Patent
Hagen

(10) Patent No.: US 12,408,674 B2
(45) Date of Patent: Sep. 9, 2025

(54) METHODS AND COMPOSITIONS FOR CONTROLLING PLANT VIRAL INFECTION

(71) Applicant: Monsanto Technology LLC, St. Louis, MO (US)

(72) Inventor: Charles Hagen, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 1118 days.

(21) Appl. No.: 16/977,038

(22) PCT Filed: Mar. 8, 2019

(86) PCT No.: PCT/US2019/021363
§ 371 (c)(1),
(2) Date: Aug. 31, 2020

(87) PCT Pub. No.: WO2019/173721
PCT Pub. Date: Sep. 12, 2019

(65) Prior Publication Data
US 2020/0404928 A1 Dec. 31, 2020

Related U.S. Application Data

(60) Provisional application No. 62/641,162, filed on Mar. 9, 2018.

(51) Int. Cl.
*A01N 63/60* (2020.01)
*A01N 25/30* (2006.01)
*C12N 15/113* (2010.01)

(52) U.S. Cl.
CPC ............. *A01N 63/60* (2020.01); *A01N 25/30* (2013.01); *C12N 15/113* (2013.01)

(58) Field of Classification Search
CPC ..................................... A01N 63/60
USPC ........................................ 800/279
See application file for complete search history.

(56) References Cited

U.S. PATENT DOCUMENTS

2015/0313238 A1* 11/2015 Hemmes ................ A01N 57/16
435/235.1
2017/0356004 A1   12/2017 Huang et al.

OTHER PUBLICATIONS

Thomas et al. The Plant Journal 25(4):417-425 (Year: 2001).*
Aguilar et al. Arch. Virol. 147 (10), 2009-2015 (Year: 2002).*
Extended European Search Report and Written Opinion regarding European App. No. 19764110.3, dated Oct. 29, 2021.
GenBank Accession No. AF484251.1, dated Mar. 18, 2005.
GenBank Accession No. AB304848.1, dated Mar. 1, 2008.
GenBank Accession No. AY789138.1, dated Dec. 20, 2005.
GenBank Accession No. AB219105.1, dated Dec. 21, 2005.
GenBank Accession No. AB353071.1, dated Jan. 27, 2009.
GenBank Accession No. AB546335.1, dated Jul. 25, 2016.
GenBank Accession No. AJ620114.1, dated Nov. 14, 2006.
GenBank Accession No. AJ633822.2, dated Jul. 5, 2005.
GenBank Accession No. AM745758.1, dated Oct. 23, 2008.
GenBank Accession No. AY366207.2, dated Dec. 11, 2008.
GenBank Accession No. AY366208.1, dated Apr. 23, 2004.
GenBank Accession No. AY366209.1, dated Apr. 23, 2004.
GenBank Accession No. AY707100.1, dated Oct. 18, 2005.
GenBank Accession No. AY863024.1, dated Mar. 9, 2007.
GenBank Accession No. D00344.1, dated May 29, 2002.
GenBank Accession No. D12517.1, dated Jan. 25, 2013.
GenBank Accession No. D13747.1, dated Oct. 31, 2007.
GenBank Accession No. D13957.1, dated Feb. 3, 1999.
GenBank Accession No. D26017.1, dated May 30, 2008.
GenBank Accession No. DQ660333.1, dated Dec. 19, 2007.
GenBank Accession No. FJ670570.2, dated Nov. 14, 2011.
GenBank Accession No. JN835466.1, dated Feb. 21, 2012.
GenBank Accession No. KJ711908.1, dated Oct. 13, 2014.
GenBank Accession No. M62730.1, dated Aug. 2, 1993.
GenBank Accession No. NC_034375.1, dated Aug. 13, 2018.
GenBank Accession No. U23414.1, dated May 4, 1996.
GenBank Accession No. X06728.1, dated Sep. 12, 1993.
GenBank Accession No. Z21647.1, dated Nov. 14, 2006.
GenBank Accession No. AB206396.1, dated May 31, 2006.
GenBank Accession No. U62963.1, dated May 19, 1997.
GenBank Accession No. S73580.1, dated Mar. 2, 1995.
GenBank Accession No. AB066288.1, dated Dec. 15, 2007.
GenBank Accession No. JN389521.1, dated Mar. 17, 2014.
GenBank Accession No. D29630.1, dated Jan. 30, 2003.
GenBank Accession No. AF308158.2, dated Apr. 23, 2004.
Spence et al., "Effect of Pepino mosaic virus on the yield and quality of glasshouse-grown tomatoes in the UK," Plant Pathology, 55: 595-606 (2006).
Konakalla et al., "Exogenous application of double-stranded RNA molecules from TMV p126 and CP genes confers resistance against TMV in tobacco," Planta, DOI 10.1007/s00425-016-2567-6 (2016).
International Search Report and Written Opinion for International Application No. PCT/US2019/021363 mailed Aug. 16, 2019.

* cited by examiner

*Primary Examiner* — Li Zheng
(74) *Attorney, Agent, or Firm* — Dentons US LLP; Judith Koehler

(57) ABSTRACT

Methods and compositions for treatment and prevention of Potexvirus disease in plants are provided, including methods and compositions employing double-stranded RNA polynucleotides and a transfer agent. Further provided are compositions for treatment or prevention of Potexvirus disease in plants, and methods for reducing expression of a Potexvirus gene and for identifying polynucleotides useful in modulating gene expression in plant viruses.

12 Claims, 12 Drawing Sheets
Specification includes a Sequence Listing.

FIG. 3

| Treatment | Disease Score Index |
|---|---|
| TECHN. POS CTRL | ~7 |
| RNA-PePMV21 | ~5 (STATISTICALLY BEST TREATMENT) |
| RNA-PePMV20 | ~7 |
| RNA-PePMV19 | ~8 |
| RNA-PePMV18 | ~8 |
| RNA-PePMV17 | ~8 |
| RNA-PePMV16 | ~8 |
| RNA-PePMV15 | ~8 |
| RNA-PePMV14 | ~8 |
| RNA-PePMV13 | ~8 |
| RNA-PePMV12 | ~8 |
| RNA-PePMV11 | ~7 |
| RNA-PePMV10 | ~7 |
| RNA-PePMV09 | ~6 |
| RNA-PePMV08 | ~7 |
| RNA-PePMV07 | ~6 |
| RNA-PePMV06 | ~6 |
| RNA-PePMV05 | ~8 |
| RNA-PePMV04 | ~7 |
| RNA-PePMV03 | ~7 |
| RNA-PePMV02 | ~8 |
| RNA-PePMV01 | ~7 |
| RNA-GFP | ~7 |
| PePMV ONLY | ~8 |
| *NOT INOC. CTRL* | ~1 |
| *BUFFER ONLY* | ~1 |

WITH CONTROL DUNNETT'S 0.05

COLUMN 1

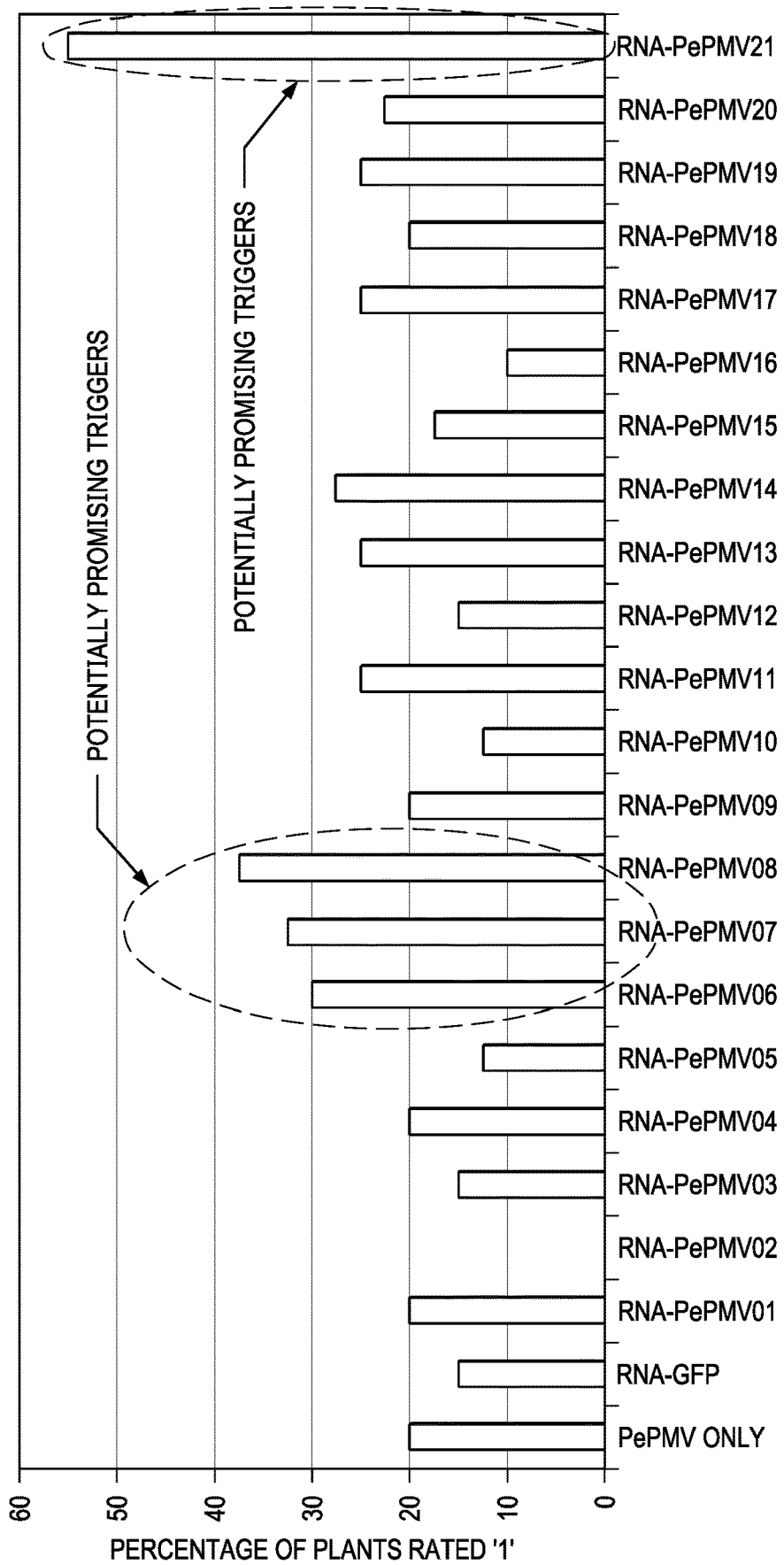

SEQUENCE LISTING

<160> NUMBER OF SEQ ID NOS: 20

<210> SEQ ID NO 1
<211> LENGTH: 298
<212> TYPE: DNA
<213> ORGANISM: Pepino mosaic virus

<400> SEQUENCE: 1

```
ggaaaacaaa ataaataaat aaatatacaa agttaaacta acacaacata accacgtgga      60
aaaacagcga aagcacttta ccacattatg tctcgtgtta gaaatacttt ggaaaagatc     120
agagacccac aagtacagtc cagcatttgt gaagctgcct atcaacatgt tcgacctgta    180
cttaaagaat ctctaatcaa ttgtccttac gcgcttaatg attatgaagc agacacccctt   240 gagaatcttg gtgtcacaat taaccccccat gcaatccaaa cacacacaca tgccgcac     298
```

<210> SEQ ID NO 2
<211> LENGTH: 300
<212> TYPE: DNA
<213> ORGANISM: Artificial sequence
<220> FEATURE:
<223> OTHER INFORMATION: Probe

<400> SEQUENCE: 2

```
gaaggctacg tccaggagcg caccatcttc ttcaaggacg acggcaacta caagacccgc      60
gccgaggtga agttcgaggg cgacaccctg gtgaaccgca tcgagctgaa gggcatcgac    120
ttcaaggagg acggcaacat cctggggcac aagctggagt acaactacaa cagccacaac    180
gtctatatca tggccgacaa gcagaagaac ggcatcaagg tgaacttcaa gatccgccac    240
aacatcgagg acggcagcgt gcagctcgcc gaccactacc agcagaacac ccccatcggc    300
```

<210> SEQ ID NO 3
<211> LENGTH: 158
<212> TYPE: DNA
<213> ORGANISM: Pepino mosaic virus

<400> SEQUENCE: 3

```
gatgcctgac acaacacctg ttgctgccac ttcaagtgca ccacccacag ccaaagatgc      60
tggtgccaaa gctccttctg acttctcaaa tcccaataca gctcctagtc tcagtgattt    120
gaagaaagtc aagtatgtct ccaccgtgac ctccgtgc                             158
```

<210> SEQ ID NO 4
<211> LENGTH: 158
<212> TYPE: DNA
<213> ORGANISM: Pepino mosaic virus

<400> SEQUENCE: 4

```
gccacaccag ctgaaattga agccctaggc aaaatcttca ccgctatggg ccttgccgcc      60
aatgagactg gtccggccat gtgggatcta gctcgtgcat atgctgatgt gcagagttct    120
aaatcggcac agctgattgg agctacccct tccaaccc                             158
```

<210> SEQ ID NO 5
<211> LENGTH: 109
<212> TYPE: DNA
<213> ORGANISM: Pepino mosaic virus

<400> SEQUENCE: 5

```
gtgcactatc acgccgagcc cttgctgctc agtttgatcg aatcaatata accccccaggc     60 aattttgcat gtactttgcc aaagttgttt ggaacatact tctcgacag                 109
```

<210> SEQ ID NO 6
<211> LENGTH: 108
<212> TYPE: DNA
<213> ORGANISM: Pepino mosaic virus

<400> SEQUENCE: 6
gaaatttgct gcatttgact tcttcgatgg agtcaccaac cctgccagcc tgcagcctgc 60
tgatggtctt atcaggcagc caaatgaaaa agaactagct gctcactc 108

<210> SEQ ID NO 7
<211> LENGTH: 153
<212> TYPE: DNA
<213> ORGANISM: Pepino mosaic virus

<400> SEQUENCE: 7
gatattacca cacttggaga agtcacacgt ggacacatgg gaggagctaa caccatgtac 60
gcgatagacg cacccccctga actttaaaca ctcgaaactt aatcagagtg gggttttcta 120
cagtttattt tcctaattat ttctttgaaa tac 153

<210> SEQ ID NO 8
<211> LENGTH: 158
<212> TYPE: DNA
<213> ORGANISM: Pepino mosaic virus

<400> SEQUENCE: 8
gattatatta ccacacttgg agaagtcaca cgtggacaca tgggaggagc taacaccatg 60
tacgcgatag acgcaccccc tgaactttaa acactcgaaa cttaatcaga gtggggtttt 120
ctacagttta ttttcctaat tatttctttg aaataaac 158

<210> SEQ ID NO 9
<211> LENGTH: 154
<212> TYPE: DNA
<213> ORGANISM: Pepino mosaic virus

<400> SEQUENCE: 9
ggtcacggaa ggaaaataat gtgcagcaaa ctactcatga ttaccatgca gtttttgaca 60
cagctcagag ctccggagat ctcccatgga aagcatggat tccacttctg aatgcacacg 120
gcttcaaggg agaccaactt caatacagtc cggc 154

<210> SEQ ID NO 10
<211> LENGTH: 154
<212> TYPE: DNA
<213> ORGANISM: Pepino mosaic virus

<400> SEQUENCE: 10
gggatggcaa agtgattcag ccaatccagg acatcaataa caaaacacca agatctgagt 60
acccatccag cattcctgca gatcttgtga atacactgcg aaacattaaa agagcagtgt 120
atgccattcc tattagccat cgaagggcaa cggc 154

<210> SEQ ID NO 11
<211> LENGTH: 108
<212> TYPE: DNA
<213> ORGANISM: Pepino mosaic virus

<400> SEQUENCE: 11

```
gggtgcttac agctctgata tcaaaaacaa taggaccggc aaattactct gttcccaatc    60
aaaagaatgg agggaaagtt ttgctttcaa aatgcaacat gaagacat                108
```

<210> SEQ ID NO 12
<211> LENGTH: 109
<212> TYPE: DNA
<213> ORGANISM: Pepino mosaic virus

<400> SEQUENCE: 12

```
gaaatcacaa gcattacaaa actttctcag aactcttggc gactctaatg actgctgcac    60
agtggttgtg ccaactgttg aactcagaaa tgattgggtg aacaaattg                109
```

<210> SEQ ID NO 13
<211> LENGTH: 154
<212> TYPE: DNA
<213> ORGANISM: Pepino mosaic virus

<400> SEQUENCE: 13

```
ggaatgattc aaccaggatt cccagttgtt atctttgatg actacactaa attgccacct    60
ggttacattg aagcctattt gttccaccat gccaacactg aacttttcat tcttactgga   120
gactcgcggc aaagtgtata tcatgagtcc aacc                                154
```

<210> SEQ ID NO 14
<211> LENGTH: 152
<212> TYPE: DNA
<213> ORGANISM: Pepino mosaic virus

<400> SEQUENCE: 14

```
gacaatgaag catacattgc ctcattagat gaagccgtcg cttattatgc taactactgt    60
ggattttacc taaatgctac acacagaaat gttcgcagtt tggccaataa gctaggtgtt   120
tacagtgaga agaaggtca cctcaaaatt cc                                  152
```

<210> SEQ ID NO 15
<211> LENGTH: 298
<212> TYPE: DNA
<213> ORGANISM: Pepino mosaic virus

<400> SEQUENCE: 15

```
ggaaaacaaa ataaataaat aaatatacaa agttaaacta acacaacata accacgtgga    60
aaaacagcga aagcacttta ccacattatg tctcgtgtta gaaatacttt ggaaaagatc   120
agagacccac aagtacagtc cagcatttgt gaagctgcct atcaacatgt tcgacctgta   180
cttaaagaat ctctaatcaa ttgtccttac gcgcttaatg attatgaagc agacaccctt   240
gagaatcttg gtgtcacaat taaccccccat gcaatccaaa cacacacaca tgccgcac    298
```

<210> SEQ ID NO 16
<211> LENGTH: 4320
<212> TYPE: DNA
<213> ORGANISM: Pepino mosaic virus

<400> SEQUENCE: 16

```
atgtctcgtg ttagaaatac tttggaaaag atcagagacc cacaagtaca gtccagcatt    60
tgtgaagctg cctatcaaca tgttcgacct gtacttaaag aatctctaat caattgtcct   120
tacgcgctta atgattatga agcagacacc cttgagaatc ttggtgtcac aattaacccc   180
```

-continued

```
catgcaatcc aaacacacac acatgccgca gccaaagtag tcgaaaatcg tatgcttgaa    240
attgttggac atcacttgcc taaagatgaa aaagtaactt tcatcttcct caaacgtagc    300
aagctgcgtt acatgagaag agctgctgtg cataaagatg tctttgtcaa tcataacatt    360
gaaccaaaag acttcttcag gtatgatgaa gagtctacat caaccagctt ttccgttgat    420
acgagaatcg catacatttc agattctcta cactttatgg aacctgctga tgtgactcac    480
ttgtttgacc gttgccaaaa ccttaaaaca ttgatggcaa ctgttgtact acctgtggaa    540
gctatacaca gacagacatc tctattccct gcgatttact ccattaacta caatgaagaa    600
ggctttgagt atatcccagg atcacacggt ggtggggcat atttccacaa atatgaaacc    660
ctagaatggc tcaaatactc tagattcatt ggacatgatc cattgactgg tttaaaatac    720
accattacga ttcaaatggt ggagagtctt ggtgccaacc acctttttcct cttccaaaga    780
ggaaactttg agacgccgct atacaggacg tttcaaaaga atagttttgt gacattccca    840
aatatattcc atccccgaca cgtcaatgcc acaaaaccta tgcctagatc aagggccata    900
cagctgtact tatatgtgaa atcagtaaat aaagttacgc aaagagatat atttgccaag    960
gttagacaac tgatttccac tgctgagcta gaattgtatg accctgatga actcacgcac   1020
gttgtaaatt atttcacata tgtgtcacaa ctgtcatcta tcaatgatta tgacaacatg   1080
ctcaaatcca gtttcttcaa aaaactggtt gcacccatgc aacacgactg gaggtgcatg   1140
attgaattct tccggggaaa gagtgacttc aatcaactgc tcacagctct tcaatggaaa   1200
gattttttcct atactattaa gactgaagag cttgtaatta ctacacacac tgctatagga   1260
caagcaataa gcaatgcagc taccacatat aaagaaagaa ggcagctgac tcaattggtc   1320
aaaaaaggta caatatcctt agcagatttt gaacagagag aacctgaaat aacttacact   1380
gagtttgagc ctgaaactag gccccaagtg gactgcgtta ctaattataa taatgcagta   1440
aaaaatttag gtcttttctgc acttgatgaa cagcctcaat gttcatcttc tagcagtcat   1500
atacctgca atgaaatatc cttagcaatg actgatgacg acaatgctgc ggccattcat   1560
gaaattgaat ctctattgtc tgaaccgata atagctcctc aactcccagc attgccacac   1620
aagacatggg ccagttatgc ttcagacact tcatccatga agaaccgtga gattgagaac   1680
ataattgctg agcttgaaat ctcacggaag gaaaataatg tgcagcaaac tactcatgat   1740
taccatgcag ttttttgacac agctcagagc tccggagatc tcccatggaa agcatggatt   1800
ccacttctga atgcacacgg cttcaaggga gaccaacttc aatacagtcc ggatggcaaa   1860
gtgattcagc caatccagga catcaataac aaaacaccaa gatctgagta cccatccagc   1920
attcctgcag atcttgtgaa tacactgcga acattaaaaa gagcagtgta tgccattcct   1980
attagccatc gaagggcaag tgcttacagc tctgatatca aaaacaatag gaccggcaaa   2040
ttactctgtt cccaatcaaa agaatggagg gaaagttttg ctttcaaaat gcaacatgaa   2100
gacatcgtta aatctggagt agtcattcat ggctgtggcg gctctggaaa atcacaagca   2160
ttacaaaact ttctcagaac tcttggcgac tctaatgact gctgcacagt ggttgtgcca   2220
actgttgaac tcagaaatga ttgggtgaac aaattgtgta agctacccat ggaacacatt   2280
aaaacatttg aaaaagcaat gattcaacca ggattcccag ttgttatctt tgatgactac   2340
actaaattgc cacctggtta cattgaagcc tatttgttcc accatgccaa cactgaactt   2400
ttcattctta ctggagactc gcggcaaagt gtatatcatg agtccaacaa tgaagcatac   2460
attgcctcat tagatgaagc cgtcgcttat tatgctaact actgtggatt ttacctaaat   2520
gctacacaca gaaatgttcg cagtttggcc aataagctag gtgtttacag tgagaaagaa   2580
```

-continued

```
ggtcacctca aaattacctt tgcctcaaat gctctacaaa agtgcaaagt gccaattttg    2640
gtgccctctc aaatgaagaa gagtgctatg caagacatag gcacaaagc catgacctac     2700 gctgggtgtc aagggcttac tgcaccgaga gtccaaattt gcttgacaa ccacacacaa     2760 cactgctcag acagggtgct gtacacttgt ctctccagag ctgtggattc catccacttt    2820
atcaatacag gcccaaacaa ttctgaattt tgggacaagc ttgaggcaac accatacctc    2880
aaagcattta ttgatactta cagagatgag aaaacagaaa tgctcaattc taagcctgct    2940
gatgacagtc ccgctgagcc tgaagctcca ttgactcact ttccagtgtc aaacggcaat    3000
aacttggaaa agttagcttc agcgcttcct gaaaaatttg caagagagtt atatgataaa    3060
caccatggat attctaatac aatccaaact gaaaatccag tggtgcaact tttccagcat    3120
caacaagcca aagatgaaac acttttctgg caacaatag aagctagact ttctattaca     3180
actccggaag ccaacttacg agaatttgtg ctaaagaaag atgttggaga tatcttgttt    3240
ttcaattacc acaatgtcat gtgcttacct gccgacccag tggatttcga gccaagaaca    3300
tgggaaatat gtgctgctga agttaaaaat acatacttag ccaaaccaat ggctaacttg    3360
atcaatgctg ctagcagaca atctcctgat ttcgacgcta acaaaatttc cctgttccta    3420
aaatctcaat gggtcaagaa agtggaaaaa ttaggtgctg tcaagtcaaa gcctggccag    3480
accattgcag ctttcatgca acaaacagtg atgttgtatg ggaccatggc cagatacctc    3540
agaaagatga gacaaagatt tcaaccaaaa catattttca tcaattgtga aacaacaact    3600
gataatctga accaatttgt taaacaaggt tggaacttta acagaacagc tcagacaaat    3660
gatttcacag cttttgacca atcacaagat ggtgcaatgc ttcaatttga agtcatgaag    3720
gcaaaattct tcaatatccc tgccgacatc attgaaggat acatcaacat caaattgaac    3780
gccaaaattt ttcttggcac attgtccatt atgaggttgt ctggtgaagg tccaactttt    3840
gatgccaaca cagaatgttc aatagcatat actgctacaa gataccatct tgattctaca    3900
gtcaagcagg tttatgctgg agatgatatg gcattagatg gagttgtcca agaaaaaccc    3960
tcttttaaaa aactacagaa caagcttaaa ctcacctcaa agacactatt tccaaaacag    4020
gttaaaggtg attatgctga attctgtggt tggactttca ctcctggtgg tatcattaaa    4080 aacccttga aaatgcatgc ttccattatg ttgcaagagg caatcggcaa tttacacact     4140
gctgccagat catatgccat tgacatgaaa cattcatacc aaatgggtga tgagctgcac    4200
aattacttaa caccagatga agctgaacaa cacttccttg ctgttcggaa gttgcacaag    4260
ttacaccaag gagaagcaat gagacttggt gaaagagcc ctccaaaagc aacacattga     4320
```

<210> SEQ ID NO 17
<211> LENGTH: 714
<212> TYPE: DNA
<213> ORGANISM: Pepino mosaic virus

<400> SEQUENCE: 17
atgcctgaca caacacctgt tgctgccact tcaagtgcac cacccacagc caaagatgct 60
ggtgccaaag ctccttctga cttctcaaat cccaatacag ctcctagtct cagtgatttg 120
aagaaagtca agtatgtctc caccgtgacc tccgtggcca caccagctga aattgaagcc 180

-continued

```
ctaggcaaaa tcttcaccgc tatgggcctt gccgccaatg agactggtcc ggccatgtgg    240
gatctagctc gtgcatatgc tgatgtgcag agttctaaat cggcacagct gattggagct    300
accccttcca accctgcact atcacgccga gcccttgctg ctcagtttga tcgaatcaat    360
ataacccccg gcaattttg catgtacttt gccaaagttg tttggaacat acttctcgac     420
agcaacattc caccagcaaa ttgggccaaa cttggttacc aagaagatac aaaatttgct    480
gcatttgact tcttcgatgg agtcaccaac cctgccagcc tgcagcctgc tgatggtctt    540
atcaggcagc caaatgaaaa agaactagct gctcactccg tagctaagta cggcgccttg    600
gctaggcaaa agatctccac aggtaattat attaccacac ttggagaagt cacacgtgga    660
cacatgggag gagctaacac catgtacgcg atagacgcac cccctgaact ttaa          714
```

```
<210> SEQ ID NO 18
<211> LENGTH: 300
<212> TYPE: DNA
<213> ORGANISM: Pepino mosaic virus

<400> SEQUENCE: 18
gtcacggaag gaaaataatg tgcagcaaac tactctcatgat taccatgcag tttttgacac    60
agctcagagc tccggagatc tcccatggaa agcatggatt ccacttctga atgcacacgg    120
cttcaaggga gaccaacttc aatacagtcc ggatggcaaa gtgattcagc caatccagga    180
catcaataac aaaacaccaa gatctgagta cccatccagc attcctgcag atcttgtgaa    240
tacactgcga acattaaaa gagcagtgta tgccattcct attagccatc gaagggcaac     300
```

```
<210> SEQ ID NO 19
<211> LENGTH: 300
<212> TYPE: DNA
<213> ORGANISM: Pepino mosaic virus

<400> SEQUENCE: 19
ggtgcttaca gctctgatat caaaaacaat aggaccggca aattactctg ttcccaatca      60
aaagaatgga gggaaagttt tgcttcaaa atgcaacatg aagacatcgt taaatctgga    120
gtagtcattc atggctgtgg cggctctgga aaatcacaag cattacaaaa ctttctcaga    180
actcttggcg actctaatga ctgctgcaca gtggttgtgc caactgttga actcagaaat    240
gattgggtga acaaattgtg taagctaccc atggaacaca ttaaaacatt tgaaaaagcc    300
```

```
<210> SEQ ID NO 20
<211> LENGTH: 300
<212> TYPE: DNA
<213> ORGANISM: Pepino mosaic virus

<400> SEQUENCE: 20
gaatgattca accaggattc ccagttgtta tctttgatga ctacactaaa ttgccacctg     60
gttacattga agcctatttg ttccaccatg ccaacactga acttttcatt cttactggag    120
actcgcggca aagtgtatat catgagtcca acaatgaagc atacattgcc tcattagatg    180
aagccgtcgc ttattatgct aactactgtg gattttacct aaatgctaca cacagaaatg    240
ttcgcagttt ggccaataag ctaggtgttt acagtgagaa agaaggtcac ctcaaaattc    300
```

METHODS AND COMPOSITIONS FOR CONTROLLING PLANT VIRAL INFECTION

CROSS-REFERENCE TO RELATED APPLICATIONS

This application is a 371 National Stage Application of PCT Application No. PCT/US2019/021363, filed Mar. 8, 2019, which application claims the benefit of priority of U.S. Provisional Application No. 62/641,162, filed Mar. 9, 2018, the disclosures of which are hereby incorporated by reference in their entireties.

FIELD OF THE INVENTION

The methods and compositions provided generally relate to the field of plant disease control and more specifically to methods and compositions for treating or preventing symptoms associated with plant Potexvirus infection.

INCORPORATION OF SEQUENCE LISTING

The sequence listing that is contained in the file named "MONS424WO_ST25.txt," which is 12.9 KB as measured in Microsoft Windows® operating system and was created on Mar. 7, 2019, is filed electronically herewith and incorporated herein by reference.

BACKGROUND

Plant viruses of the genus Potexvirus are economically important, causing reduced vegetative output and sometimes death of infected plants. Growers seeking to protect their crops from Potexviruses such as Pepino mosaic virus (PepMV) have traditionally attempted to guard their crops from mechanical transmission of infection. However, because these strategies have had limited success, and are expensive and labor intensive, alternative strategies for controlling Potexviruses infection are needed.

SUMMARY

In a first aspect, methods of treatment or prevention of a Pepino Mosaic Virus (PepMV) infection in a plant are provided, the methods comprising topically applying to said plant a composition comprising a double-stranded RNA polynucleotide and a transfer agent, wherein the double-stranded RNA polynucleotide is complementary to all or a portion of an essential PepMV gene sequence or an RNA transcript thereof, wherein the essential PepMV gene is from the PepMV genome 5' region, is the PepMV RNA-dependent RNA polymerase (RdRp) gene or is the PepMV capsid protein (CP) gene and wherein the symptoms of viral infection or development of symptoms are reduced or eliminated in said plant relative to a plant not treated with said composition when grown under the same conditions. In certain embodiments, said transfer agent is an organosilicone surfactant composition or compound contained therein. In some embodiments, said essential gene sequence is selected from the group consisting of SEQ ID NOs: 15-17, and a fragment thereof. In further embodiments, said double-stranded RNA polynucleotide is complementary to a fragment comprising at least 18 contiguous nucleotides of any of SEQ ID NOs: 15-17. In specific embodiments, said double-stranded RNA polynucleotide comprises a sequence selected from the group consisting of: a) a sequence of any of SEQ ID NOs: 1, 18, 19, 20, 14, 8, and 7, and b) a fragment of any of SEQ ID NOs: 1, 18, 19, 20, 14, 8, and 7. Compositions provided herein include double-stranded RNA polynucleotides complementary to all or a portion of at least two essential PepMV gene sequences or an RNA transcript thereof. In certain embodiments, said essential gene sequence is selected from the group consisting of SEQ ID NOs: 15-17, and a fragment thereof. Said composition may be topically applied by spraying, dusting, or applied to the plant surface as matrix-encapsulated RNA.

In a further aspect, compositions are provided comprising a double-stranded RNA polynucleotide and a transfer agent, wherein the double-stranded RNA polynucleotide is complementary to all or a portion of an essential PepMV gene sequence or an RNA transcript thereof, wherein the essential PepMV gene is from the PepMV genome 5' region, is the PepMV RNA-dependent RNA polymerase (RdRp) gene or is the PepMV capsid protein (CP) gene, and wherein topical application of the composition to a plant reduces or eliminates the symptoms of PepMV infection or development in said plant relative to a plant not treated with said composition when grown under the same conditions. In certain embodiments, the transfer agent is an organosilicone composition. In some embodiments, the essential gene sequence is selected from the group consisting of SEQ ID NOs: 15-17, and a fragment thereof. In other embodiments, the double-stranded RNA polynucleotide is complementary to a fragment comprising at least 18 contiguous nucleotides of any of SEQ ID NOs: 15-17. In certain examples, said double-stranded RNA polynucleotide comprises a sequence selected from the group consisting of: a) a sequence of any of SEQ ID NOs: 1, 18, 19, 20, 14, 8, and 7, and b) a fragment of any of SEQ ID NOs: 1, 18, 19, 20, 14, 8, and 7. In certain embodiments, compositions provided herein are further defined as comprising double-stranded RNA polynucleotides complementary to all or a portion of at least two essential PepMV gene sequences or an RNA transcript thereof.

In another aspect, methods are provided of reducing expression of an essential PepMV gene comprising contacting a PepMV particle with a composition comprising a double-stranded RNA polynucleotide, wherein the double-stranded RNA polynucleotide is complementary to all or a portion of an essential PepMV gene sequence or an RNA transcript thereof. In some embodiments, the essential PepMV gene is from the PepMV genome 5' region, is the PepMV RNA-dependent RNA polymerase (RdRp) gene or is the PepMV capsid protein (CP) gene. In some embodiments, the composition further comprises a transfer agent. In some embodiments, the transfer agent is an organosilicone compound. In further embodiments, said double-stranded RNA polynucleotide is complementary to a fragment comprising at least 18 contiguous nucleotides of any of SEQ ID NOs: 15-17. In certain examples, said double-stranded RNA polynucleotide comprises a sequence selected from the group consisting of: a) a sequence of any of SEQ ID NOs: 1, 18, 19, 20, 14, 8, and 7, and b) a fragment of any of SEQ ID NOs: 1, 18, 19, 20, 14, 8, and 7. In certain embodiments, said composition comprises double-stranded RNA polynucleotides complementary to all or a portion of at least two essential PepMV gene sequences or an RNA transcript thereof. In some embodiments, the composition may be applied to a surface of a plant.

In yet a further aspect, methods are provided of identifying double-stranded RNA polynucleotides useful in modulating PepMV gene expression when topically treating a plant comprising: a) providing a plurality of double-stranded RNA polynucleotides that comprise a region complementary to all or a part of an essential PepMV gene or RNA transcript thereof; b) topically treating said plant with one or more of said double-stranded RNA polynucleotides and a transfer agent; c) analyzing said plant or extract for modulation of symptoms of PepMV infection; and d) selecting a double-stranded RNA polynucleotide capable of modulating the symptoms or occurrence of PepMV infection. In certain embodiments, said transfer agent is an organosilicone compound. In certain embodiments, the transfer agent is an abrasive.

Several embodiments described herein relate to an agricultural composition comprising a double-stranded RNA polynucleotide, wherein the double-stranded RNA polynucleotide is complementary to all or a portion of an essential PepMV gene sequence or an RNA transcript thereof. In some embodiments, the essential PepMV gene is from the PepMV genome 5' region. In some embodiments, the essential PepMV gene is the PepMV RNA-dependent RNA polymerase (RdRp) gene or is the PepMV capsid protein (CP) gene. In some embodiments the agricultural composition comprises a transfer agent. In certain embodiments, the transfer agent is an organosilicone surfactant composition or compound contained therein. In some embodiments, said essential gene sequence is selected from the group consisting of SEQ ID NOs: 15-17, and a fragment thereof. In further embodiments, said double-stranded RNA polynucleotide is complementary to a fragment comprising at least 18 contiguous nucleotides of any of SEQ ID NOs: 15-17. In specific embodiments, said double-stranded RNA polynucleotide comprises a sequence selected from the group consisting of: a) a sequence of any of SEQ ID NOs: 1, 18, 19, 20, 14, 8, and 7, and b) a fragment of any of SEQ ID NOs: 1, 18, 19, 20, 14, 8, and 7. Compositions provided herein include double-stranded RNA polynucleotides complementary to all or a portion of at least two essential PepMV gene sequences or an RNA transcript thereof. In certain embodiments, said essential gene sequence is selected from the group consisting of SEQ ID NOs: 15-17, and a fragment thereof. In some embodiments, the agricultural composition may be topically applied to a plant by spraying, dusting, or applied to a plant surface as matrix-encapsulated RNA.

In another aspect, agricultural chemical compositions are provided comprising an admixture of a composition provided herein and a pesticide. In certain examples, said pesticide is selected from the group consisting of anti-viral compounds, insecticides, fungicides, nematocides, bactericides, acaricides, growth regulators, chemosterilants, semiochemicals, repellents, attractants, pheromones, feeding stimulants, and biopesticides.

In a further aspect, methods of treatment or prevention of a PepMV infection in a plant are provided comprising: topically applying to said plant a composition comprising an antisense single-stranded DNA polynucleotide, wherein said antisense single-stranded DNA polynucleotide is complementary to all or a portion of an essential PepMV gene sequence or an RNA transcript thereof wherein the symptoms of viral infection or development of symptoms are reduced or eliminated in said plant relative to a plant not treated with said composition when grown under the same conditions. In some embodiments, the essential PepMV gene is from the PepMV genome 5' region, is the PepMV RNA-dependent RNA polymerase (RdRp) gene or is the PepMV capsid protein (CP) gene. In some embodiments, the composition comprises a transfer agent. In certain embodiments, the transfer agent is an organosilicone surfactant composition or compound contained therein. In some embodiments, the essential gene sequence is selected from the group consisting of SEQ ID NOs: 15-17, and a fragment thereof. In further embodiments, the single-stranded DNA polynucleotide is complementary to a fragment comprising at least 18 contiguous nucleotides of any of SEQ ID NOs: 15-17. In some embodiments, the composition may be topically applied to a plant by spraying, dusting, or applied to a plant surface as matrix-encapsulated DNA.

BRIEF DESCRIPTION OF THE DRAWINGS

The following drawings form part of the present specification and are included to further demonstrate certain aspects of the function of the compositions and methods. The function may be better understood by reference to one or more of these drawings in combination with the detailed description of specific embodiments presented herein. The function can be more fully understood from the following description of the figures:

FIG. 3: Shows the average disease index score for plants treated with the targeting sequences shown in FIG. 2.

FIG. 4: Shows the percentage of plants with a disease score index (DSI) rating of 1 when treated with the targeting sequences shown in FIG. 2.

DETAILED DESCRIPTION

Figure 1:
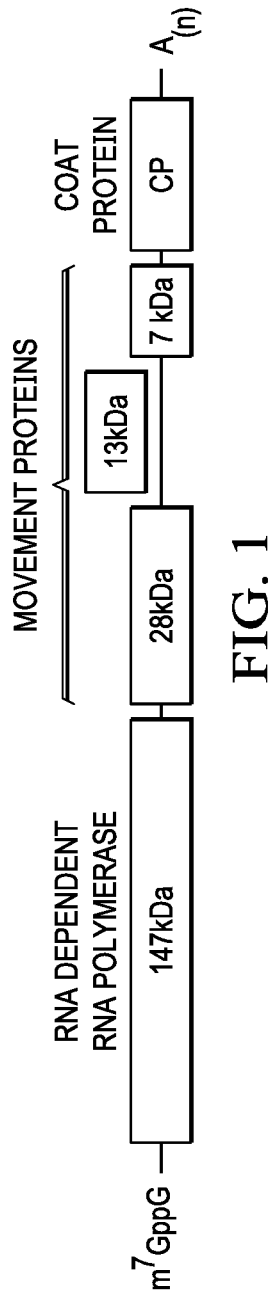
FIG. 1: Shows the position of the RNA dependent RNA polymerase (RdRp) gene, genes encoding movement proteins, and the coat or capsid protein gene (CP) within the PepMV genome.

Pepino mosaic virus (PepMV) is a species of virus of the family Flexiviridae, of the genus Potexvirus. PepMV infection is a major disease of culture-grown tomatoes, causing significant losses of marketable fruit worldwide including losses of up to a third of marketable fruit in larger commercial varieties. PepMV infection is most commonly transmitted mechanically. However, control of mechanical transmission is expensive and labor intensive, and reliable sources of genetic resistance to PepMV have not yet been identified. PepMV infection therefore remains a serious problem for commercial tomato growers.

In order to develop an effective alternative for controlling PepMV infection, the present disclosure provides novel dsRNA polynucleotides capable of effectively suppressing expression of viral genes via RNA interference (RNAi). The dsRNA polynucleotides provided herein comprise targeting sequences designed to target genetic sequences within the PepMV genome, and can be applied to a plant directly or within a formulation to treat or prevent PepMV infection under standard growing conditions. Further provided are methods of identifying targeting sequences useful in treatment or prevention of other economically significant plant viruses, including viruses that are naturally transmitted by direct plant-to-plant/rub transmission.

In certain embodiments, dsRNA polynucleotides are provided that are highly effective in preventing PepMV infection. For example, dsRNA polynucleotides are disclosed which are targeted against the 5' end of the PepMV genome, a region in the middle of the PepMV RNA-dependent RNA polymerase gene, and the 3' end of the PepMV capsid protein gene. Examples of dsRNA polynucleotides provided herein include SEQ ID NOs: 1-14 and those listed in Tables 1 and 2.

Methods are further provided for preventing or treating PepMV infection and transmission in plants within a greenhouse, growth chamber, or field environment by applying the dsRNA polynucleotides provided herein. In certain embodiments, dsRNA polynucleotides are formulated for delivery to plants or fields to include transfer agents, pesticides, or other active ingredients.

Further provided are methods of identifying dsRNA polynucleotides effective in the treatment or control of PepMV or other Potexviruses. For example, the present disclosure shows that highly effective targeting sequences from the PepMV genome can be used to develop targeting sequences effective in treating or preventing infection by other Potexviruses.

I. dsRNA Molecules for Treatment or Prevention of Potexvirus Infection

Several embodiments relate to methods and compositions for the prevention or treatment of Potexvirus infection in a plant comprising the topical administration of a dsRNA polynucleotide comprising contiguous nucleotides that are essentially identical or essentially complementary to the Potexvirus genome. In certain embodiments, dsRNA polynucleotides provided comprise at least 18 contiguous nucleotides with no more than 4 mismatches complementary to a corresponding sequence within the Potexvirus genome. In some embodiments, dsRNA polynucleotides provided comprise at least 16, at least 17, at least 18, at least 20, at least 21, at least 22, at least 23, at least 24, or at least 25 contiguous nucleotides complementary to the Potexvirus genome. In some embodiments, the dsRNA polynucleotide is essentially identical to regions of the Potexvirus genome selected from the following groups: the 5' end of the genome, the RNA dependent RNA polymerase (RdRp) gene, and the capsid protein (CP) gene. In certain examples, dsRNA polynucleotides highly effective in treating or preventing Potexvirus infection in a plant comprise SEQ ID NOs: 1-14 or sequences listed in Tables 1 or 2. In some embodiments, methods and compositions for the prevention or treatment of Potexvirus infection in a plant comprise the topical administration of polynucleotides provided herein. In certain embodiments, the methods and compositions disclosed herein provide regulation, repression, or delay and/or modulation of symptoms or disease caused by Potexvirus.

Compositions provided may include dsRNA, ssRNA, ssDNA, dsDNA, or polynucleotides designed to target single or multiple viral genes, or multiple segments of one or more viral genes, such as genes from a Potexvirus or other plant virus, including, but not limited to the viral gene sequences set forth in SEQ ID NOs:1-14 and Tables 1 and 2. In certain embodiments, any viral gene from any plant virus may be targeted by compositions provided herein. The target gene may include multiple consecutive segments of a target gene, multiple non-consecutive segments of a target gene, multiple alleles of a target gene, or multiple target genes from one or more Potexvirus species, including PepMV. In some embodiments, the polynucleotides or oligonucleotides are essentially identical or essentially complementary to a consensus nucleotide sequence.

Polynucleotides provided herein may be complementary to all or a portion of a viral gene sequence, including a promoter, intron, coding sequence, exon, 5' untranslated region, and 3' untranslated region. In specific embodiments, a polynucleotide provided herein can be cloned or identified from (a) coding (protein-encoding), (b) non-coding (promoter and other gene related molecules), or (c) both coding and non-coding parts of the target viral gene. Non-coding parts may include DNA, such as promoter regions or an RNA transcribed by the DNA that provides RNA regulatory molecules, including but not limited to: introns, cis-acting regulatory RNA elements, 5' or 3' untranslated regions, and microRNAs (miRNA), natural antisense siRNAs, and other small RNAs with regulatory function or RNAs having structural or enzymatic function including but not limited to: ribozymes, ribosomal RNAs, t-RNAs, aptamers, and riboswitches.

Viral genomes targeted by the polynucleotides provided herein include viruses of the family Flexiviridae. In certain embodiments, viruses of the genus Potexvirus are targeted including viruses selected from the group consisting of PepMV, Allium virus X, Alstroemeria virus X, Alternanthera mosaic virus, Asparagus virus 3, Bamboo mosaic virus, Cactus virus X, Cassava common mosaic virus, Cassava virus X, Clover yellow mosaic virus, Cymbidium mosaic virus, Foxtail mosaic virus, Hosta virus X, Hydrangea ringspot virus, Lagenaria mild mosaic virus, Lettuce virus X, Lily virus X, Malva mosaic virus, Mint virus X, Narcissus mosaic virus, Nerine virus X, Opuntia virus X, Papaya mosaic virus, Phaius virus X, Plantago asiatica mosaic virus, Plantain virus X, Potato aucuba mosaic virus, Potato virus X, Schlumbergera virus X, Strawberry mild yellow edge virus, Tamus red mosaic virus, Tulip virus X, White clover mosaic virus, Yam virus X, and Zygocactus virus X.

II. Methods of Treating or Preventing Potexvirus Infection

In certain aspects, methods are provided for controlling Potexvirus infection of a plant including treatment of the plant with at least a first polynucleotide targeting all or a portion of a target viral gene, wherein the polynucleotide is capable of modulation of the target gene and controlling Potexvirus infection. Certain embodiments further comprise a transfer agent that facilitates delivery of the polynucleotide to a plant, and may include solvents, diluents, a pesticide that complements the action of the polynucleotide, an herbicide or additional pesticides that provide an additional mode of action different from the polynucleotide, various salts or stabilizing agents that enhance the utility of the composition as an admixture of the components of the composition.

In some embodiments, methods provided may include one or more applications of a polynucleotide composition and one or more applications of a transfer agent for conditioning of a plant or plant virus to permeation by polynucleotides or activity or stability of the polynucleotides. The polynucleotide molecules may be ssDNA, dsDNA, ssRNA, or dsRNA oligonucleotides; or ssDNA, dsDNA, ssRNA, or dsRNA polynucleotides, chemically modified DNA oligonucleotides or polynucleotides, or mixtures thereof.

In certain embodiments, a conditioning step to increase permeability of a plant to a polynucleotide may be included. The conditioning and polynucleotide application can be performed separately or in a single step. When the conditioning and polynucleotide application are performed in separate steps, the conditioning can precede or can follow the polynucleotide application within minutes, hours, or days. In some embodiments, more than one conditioning step or more than one polynucleotide molecule application can be performed on the same plant.

III. Application of Polynucleotides to Plants

The polynucleotide compositions provided are useful in compositions, such as liquids that comprise polynucleotide molecules (e.g., ssDNA, dsDNA, ssRNA, or dsRNA polynucleotides) alone or in combination with other components either in the same liquid or in separately applied liquids that provide a transfer agent. As used herein, a transfer agent is an agent that, when combined with a polynucleotide in a composition that is topically applied to a target plant surface facilitates the uptake of the polynucleotide into the plant. In one embodiment, the transfer agent enhances the ability of the polynucleotide to enter a plant cell. In certain embodiments, a transfer agent is therefore an agent that conditions the surface of plant tissue, e. g., leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. In some embodiments, the polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof.

Embodiments of agents or treatments for conditioning of a plant to permeation by polynucleotides include emulsions, reverse emulsions, liposomes, and other micellar-like compositions. Further agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the 9$^{th}$ Compendium of Herbicide Adjuvants, publicly available on the internet at herbicide.adjuvants.com can be used, e.g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of a target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5." In certain embodiments, the average chain length "n" can vary from about 5 to about 14. Terminal groups can include, but are not limited to, alkyl groups such as a methyl group. Effective organosilicone compounds include, but are not limited to, trisiloxane ethoxylate surfactants or polyalkylene oxide modified heptamethyl trisiloxane.

In certain embodiments, an organosilicone preparation that is commercially available as Silwet® L-77 surfactant having CAS Number 27306-78-1 and EPA Number: CAL-.REG.NO. 5905-50073-AA, and currently available from Momentive Performance Materials, Albany, New York can be used to prepare a polynucleotide composition. In certain embodiments where a Silwet® L-77 organosilicone preparation is used as a pre-spray treatment of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet® L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, any of the commercially available organosilicone preparations provided such as the following Breakthru S 321, Breakthru S 200 Cat #67674-67-3, Breakthru OE 441 Cat #68937-55-3, Breakthru S 278 Cat #27306-78-1, Breakthru S 243, Breakthru S 233 Cat #134180-76-0, available from manufacturer Evonik Goldschmidt (Germany), Silwet® HS 429, Silwet® HS 312, Silwet® HS 508, Silwet® HS 604 (Momentive Performance Materials, Albany, New York) can be used as transfer agents in a polynucleotide composition. In certain embodiments where an organosilicone preparation is used as a pre-spray treatment of plant leaves or other surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Delivery of a polynucleotide can be accomplished by a variety of methods including, without limitation, (1) loading liposomes with an ssDNA, dsDNA, ssRNA, or dsRNA molecule provided herein and (2) complexing an ssDNA, dsDNA, ssRNA, or dsRNA molecule with lipids or liposomes to form nucleic acid-lipid or nucleic acid-liposome complexes. The liposome can be composed of cationic and neutral lipids commonly used to transfect cells in vitro. Cationic lipids can complex (e.g., charge-associate) with negatively charged, nucleic acids to form liposomes. Examples of cationic liposomes include, without limitation, lipofectin, lipofectamine, lipofectace, and DOTAP. Procedures for forming liposomes are well known in the art. Liposome compositions can be formed, for example, from phosphatidylcholine, dimyristoyl phosphatidylcholine, dipalmitoyl phosphatidylcholine, dimyristoyl phosphatidyl glycerol, dioleoyl phosphatidylethanolamine or liposomes comprising dihydrosphingomyelin (DHSM). Numerous lipophilic agents are commercially available, including Lipofectin® (Invitrogen/Life Technologies, Carlsbad, Calif.) and Effectene™ (Qiagen, Valencia, Calif.). In addition, systemic delivery methods can be optimized using commercially available cationic lipids such as DDAB or DOTAP, each of which can be mixed with a neutral lipid such as DOPE or cholesterol. In some cases, liposomes such as those described by Templeton et al. (*Nature Biotechnology,* 15:647-652, 1997) can be used. In other embodiments, polycations such as polyethyleneimine can be used to achieve delivery in vivo and ex vivo (Boletta et al., *J. Am Soc. Nephrol.* 7:1728, 1996). Additional information regarding the use of liposomes to deliver nucleic acids can be found in U.S. Pat. No. 6,271,359, PCT Publication WO 96/40964 and Morrissey et al. (*Nat Biotechnol.* 23(8):1002-7, 2005).

The targeting DNA or RNA polynucleotide and/or oligonucleotide molecule compositions are useful in compositions, such as liquids that comprise the polynucleotide molecules at low concentrations, alone or in combination with other components, for example one or more herbicide molecules, either in the same solution or in separately applied liquids that also provide a transfer agent. While there is no upper limit on the concentrations and dosages of polynucleotide molecules that can useful in the methods, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, or seed. In one embodiment, a useful treatment for herbaceous plants using 25-mer oligonucleotide molecules is about 1 nanomole (nmol) of oligonucleotide molecules per plant, for example, from about 0.05 to 1 nmol per plant. Other embodiments for herbaceous plants include useful ranges of about 0.05 to about 100 nmol, or about 0.1 to about 20 nmol, or about 1 nmol to about 10 nmol of polynucleotides per plant. Very large plants, trees, or vines may require correspondingly larger amounts of polynucleotides. To illustrate embodiments, the factor 1×, when applied to oligonucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The targeting polynucleotide compositions may also be used as mixtures with various agricultural chemicals and/or insecticides, miticides and fungicides, pesticidal and biopesticidal agents. Examples include, but are not limited to, azinphos-methyl, acephate, isoxathion, isofenphos, ethion, etrimfos, oxydemeton-methyl, oxydeprofos, quinalphos, chlorpyrifos, chlorpyrifos-methyl, chlorfenvinphos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridafenthion, pirimiphos-methyl, fenitrothion, fenthion, phenthoate, flupyrazophos, prothiofos, propaphos, profenofos, phoxime, phosalone, phosmet, formothion, phorate, malathion, mecarbam, mesulfenfos, methamidophos, methidathion, parathion, methyl parathion, monocrotophos, trichlorphon, EPN, isazophos, isamidofos, cadusafos, diamidaphos, dichlofenthion, thionazin, fenamiphos, fosthiazate, fosthietan, phosphocarb, DSP, ethoprophos, alanycarb, aldicarb, isoprocarb, ethiofencarb, carbaryl, carbosulfan, xylylcarb, thiodicarb, pirimicarb, fenobucarb, furathiocarb, propoxur, bendiocarb, benfuracarb, methomyl, metolcarb, XMC, carbofuran, aldoxycarb, oxamyl, acrinathrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cypermethrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox, cartap, thiocyclam, bensultap, acetamiprid, imidacloprid, clothianidin, dinotefuran, thiacloprid, thiamethoxam, nitenpyram, chlorfluazuron, diflubenzuron, teflubenzuron, triflumuron, novaluron, noviflumuron, bistrifluoron, fluazuron, flucycloxuron, flufenoxuron, hexaflumuron, lufenuron, chromafenozide, tebufenozide, halofenozide, methoxyfenozide, diofenolan, cyromazine, pyriproxyfen, buprofezin, methoprene, hydroprene, kinoprene, triazamate, endosulfan, chlorfenson, chlorobenzilate, dicofol, bromopropylate, acetoprole, fipronil, ethiprole, pyrethrin, rotenone, nicotine sulphate, BT (*Bacillus thuringiensis*) agent, spinosad, abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pyrimidifen, fenazaquin, fenothiocarb, fenpyroximate, fluacrypyrim, fluazinam, flufenzin, hexythiazox, propargite, benzomate, polynactin complex, milbemectin, lufenuron, mecarbam, methiocarb, mevinphos, halfenprox, azadirachtin, diafenthiuron, indoxacarb, emamectin benzoate, potassium oleate, sodium oleate, chlorfenapyr, tolfenpyrad, pymetrozine, fenoxycarb, hydramethylnon, hydroxy propyl starch, pyridalyl, flufenerim, flubendiamide, flonicamid, metaflumizole, lepimectin, TPIC, albendazole, oxibendazole, oxfendazole, trichlamide, fensulfothion, fenbendazole, levamisole hydrochloride, morantel tartrate, dazomet, metam-sodium, triadimefon, hexaconazole, propiconazole, ipconazole, prochloraz, triflumizole, tebuconazole, epoxiconazole, difenoconazole, flusilazole, triadimenol, cyproconazole, metconazole, fluquinconazole, bitertanol, tetraconazole, triticonazole, flutriafol, penconazole, diniconazole, fenbuconazole, bromuconazole, imibenconazole, simeconazole, myclobutanil, hymexazole, imazalil, furametpyr, thifluzamide, etridiazole, oxpoconazole, oxpoconazole fumarate, pefurazoate, prothioconazole, pyrifenox, fenarimol, nuarimol, bupirimate, mepanipyrim, cyprodinil, pyrimethanil, metalaxyl, mefenoxam, oxadixyl, benalaxyl, thiophanate, thiophanate-methyl, benomyl, carbendazim, fuberidazole, thiabendazole, manzeb, propineb, zineb, metiram, maneb, ziram, thiuram, chlorothalonil, ethaboxam, oxycarboxin, carboxin, flutolanil, silthiofam, mepronil, dimethomorph, fenpropidin, fenpropimorph, spiroxamine, tridemorph, dodemorph, flumorph, azoxystrobin, kresoxim-methyl, metominostrobin, orysastrobin, fluoxastrobin, trifloxystrobin, dimoxystrobin, pyraclostrobin, picoxystrobin, iprodione, procymidone, vinclozolin, chlozolinate, flusulfamide, dazomet, methyl isothiocyanate, chloropicrin, methasulfocarb, hydroxyisoxazole, potassium hydroxyisoxazole, echlomezol, D-D, carbam, basic copper chloride, basic copper sulfate, copper nonylphenolsulfonate, oxine copper, DBEDC, anhydrous copper sulfate, copper sulfate pentahydrate, cupric hydroxide, inorganic sulfur, wettable sulfur, lime sulfur, zinc sulfate, fentin, sodium hydrogen carbonate, potassium hydrogen carbonate, sodium hypochlorite, silver, edifenphos, tolclofos-methyl, fosetyl, iprobenfos, dinocap, pyrazophos, carpropamid, fthalide, tricyclazole, pyroquilon, diclocymet, fenoxanil, kasugamycin, validamycin, polyoxins, blasticiden S, oxytetracycline, mildiomycin, streptomycin, rape seed oil, machine oil, benthiavalicarbisopropyl, iprovalicarb, propamocarb, diethofencarb, fluoroimide, fludioxanil, fenpiclonil, quinoxyfen, oxolinic acid, chlorothalonil, captan, folpet, probenazole, acibenzolar-S-methyl, tiadinil, cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichlofluanide, triforine, isoprothiolane, ferimzone, diclomezine, tecloftalam, pencycuron, chinomethionat, iminoctadine acetate, iminoctadine albesilate, ambam, polycarbamate, thiadiazine, chloroneb, nickel dimethyldithiocarbamate, guazatine, dodecylguanidine-acetate, quintozene, tolylfluanid, anilazine, nitrothalisopropyl, fenitropan, dimethirimol, benthiazole, harpin protein, flumetover, mandipropamide and penthiopyrad.

In specific embodiments, a plant disease control composition as provided herein may further be provided in a composition formulated for application to a plant that comprises at least one other active ingredient. Examples of such active ingredients may include, but are not limited to, an insecticidal protein such as a patatin, a *Bacillus thuringiensis* insecticidal protein, a *Xenorhabdus* insecticidal protein, a *Photorhabdus* insecticidal protein, a *Bacillus laterosporous* insecticidal protein, and a *Bacillus sphearicus* insecticidal protein. In another non-limiting example, such an active ingredient is a herbicide, such as one or more of acetochlor, acifluorfen, acifluorfen-sodium, aclonifen, acrolein, alachlor, alloxydim, allyl alcohol, ametryn, amicarbazone, amidosulfuron, aminopyralid, amitrole, ammonium sulfamate, anilofos, asulam, atraton, atrazine, azimsulfuron, BCPC, beflubutamid, benazolin, benfluralin, benfuresate, bensulfuron, bensulfuron-methyl, bensulide, bentazone, benzfendizone, benzobicyclon, benzofenap, bifenox, bilanafos, bispyribac, bispyribac-sodium, borax, bromacil, bromobutide, bromoxynil, butachlor, butafenacil, butamifos, butralin, butroxydim, butylate, cacodylic acid, calcium chlorate, cafenstrole, carbetamide, carfentrazone, carfentrazone-ethyl, CDEA, CEPC, chlorflurenol, chlorflurenol-methyl, chloridazon, chlorimuron, chlorimuron-ethyl, chloroacetic acid, chlorotoluron, chlorpropham, chlorsulfuron, chlorthal, chlorthal-dimethyl, cinidon-ethyl, cinmethylin, cinosulfuron, cisanilide, clethodim, clodinafop, clodinafop-propargyl, clomazone, clomeprop, clopyralid, cloransulam, cloransulam-methyl, CMA, 4-CPB, CPMF, 4-CPP, CPPC, cresol, cumyluron, cyanamide, cyanazine, cycloate, cyclosulfamuron, cycloxydim, cyhalofop, cyhalofop-butyl, 2,4-D, 3,4-DA, daimuron, dalapon, dazomet, 2,4-DB, 3,4-DB, 2,4-DEB, desmedipham, dicamba, dichlobenil, ortho-dichlorobenzene, para-dichlorobenzene, dichlorprop, dichlorprop-P, diclofop, diclofop-methyl, diclosulam, difenzoquat, difenzoquat metilsulfate, diflufenican, diflufenzopyr, dimefuron, dimepiperate, dimethachlor, dimethametryn, dimethenamid, dimethenamid-P, dimethipin, dimethylarsinic acid, dinitramine, dinoterb, diphenamid, diquat, diquat dibromide, dithiopyr, diuron, DNOC, 3,4-DP, DSMA, EBEP, endothal, EPTC, esprocarb, ethalfluralin, ethametsulfuron, ethametsulfuron-methyl, ethofumesate, ethoxyfen, ethoxysulfuron, etobenzanid, fenoxaprop-P, fenoxaprop-P-ethyl, fentrazamide, ferrous sulfate, flamprop-M, flazasulfuron, florasulam, fluazifop, fluazifop-butyl, fluazifop-P, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, fluoroglycofen, fluoroglycofen-ethyl, flupropanate, flupyrsulfuron, flupyrsulfuron-methyl-sodium, flurenol, fluridone, fluorochloridone, fluoroxypyr, flurtamone, fluthiacet, fluthiacet-methyl, fomesafen, foramsulfuron, fosamine, glufosinate, glufosinate-ammonium, glyphosate, halosulfuron, halosulfuron-methyl, haloxyfop, haloxyfop-P, HC-252, hexazinone, imazamethabenz, imazamethabenz-methyl, imazamox, imazapic, imazapyr, imazaquin, imazethapyr, imazosulfuron, indanofan, iodomethane, iodosulfuron, iodosulfuron-methyl-sodium, ioxynil, isoproturon, isouron, isoxaben, isoxachlortole, isoxaflutole, karbutilate, lactofen, lenacil, linuron, MAA, MAMA, MCPA, MCPA-thioethyl, MCPB, mecoprop, mecoprop-P, mefenacet, mefluidide, mesosulfuron, mesosulfuron-methyl, mesotrione, metam, metamifop, metamitron, metazachlor, methabenzthiazuron, methylarsonic acid, methyldymron, methyl isothiocyanate, metobenzuron, metolachlor, S-metolachlor, metosulam, metoxuron, metribuzin, metsulfuron, metsulfuron-methyl, MK-66, molinate, monolinuron, MSMA, naproanilide, napropamide, naptalam, neburon, nicosulfuron, nonanoic acid, norflurazon, oleic acid (fatty acids), orbencarb, orthosulfamuron, oryzalin, oxadiargyl, oxadiazon, oxasulfuron, oxaziclomefone, oxyfluorfen, paraquat, paraquat dichloride, pebulate, pendimethalin, penoxsulam, pentachlorophenol, pentanochlor, pentoxazone, pethoxamid, petrolium oils, phenmedipham, phenmedipham-ethyl, picloram, picolinafen, pinoxaden, piperophos, potassium arsenite, potassium azide, pretilachlor, primisulfuron, primisulfuron-methyl, prodiamine, profluazol, profoxydim, prometon, prometryn, propachlor, propanil, propaquizafop, propazine, propham, propisochlor, propoxycarbazone, propoxycarbazone-sodium, propyzamide, prosulfocarb, prosulfuron, pyraclonil, pyraflufen, pyraflufen-ethyl, pyrazolynate, pyrazosulfuron, pyrazosulfuron-ethyl, pyrazoxyfen, pyribenzoxim, pyributicarb, pyridafol, pyridate, pyriftalid, pyriminobac, pyriminobac-methyl, pyrimisulfan, pyrithiobac, pyrithiobac-sodium, quinclorac, quinmerac, quinoclamine, quizalofop, quizalofop-P, rimsulfuron, sethoxydim, siduron, simazine, simetryn, SMA, sodium arsenite, sodium azide, sodium chlorate, sulcotrione, sulfentrazone, sulfometuron, sulfometuron-methyl, sulfosate, sulfosulfuron, sulfuric acid, tar oils, 2,3,6-TBA, TCA, TCA-sodium, tebuthiuron, tepraloxydim, terbacil, terbumeton, terbuthylazine, terbutryn, thenylchlor, thiazopyr, thifensulfuron, thifensulfuron-methyl, thiobencarb, tiocarbazil, topramezone, tralkoxydim, tri-allate, triasulfuron, triaziflam, tribenuron, tribenuron-methyl, tricamba, triclopyr, trietazine, trifloxysulfuron, trifloxysulfuron-sodium, trifluralin, triflusulfuron, triflusulfuron-methyl, trihydroxytriazine, tritosulfuron, [3-[2-chloro-4-fluoro-5-(-methyl-6-trifluoromethyl-2,4-dioxo-,2,3,4-tetrahydropyrimidin-3-yl)phenoxyl-2-pyridyloxy]acetic acid ethyl ester (CAS RN 353292-3-6), 4-[(4,5-dihydro-3-methoxy-4-methyl-5-oxo)-H-,2,4-triazolylcarbonyl-sulfamoyl]-5-methyl-thiophene-3-carboxylic acid (BAY636), BAY747 (CAS RN 33504-84-2), topramezone (CAS RN 2063-68-8), 4-hydroxy-3-[[2-[(2-methoxyethoxy)methyl]-6-(trifluoro-methyl)-3-pyridi-nyl]carbonyl]-bicyclo[3.2]oct-3-en-2-one (CAS RN 35200-68-5), and 4-hydroxy-3-[[2-(3-methoxypropyl)-6-(difluoromethyl)-3-pyridinyl]carbon-yl]-bicyclo[3.2.1]oct-3-en-2-one.

It is contemplated that the compositions provided may contain multiple DNA or RNA polynucleotides and/or pesticides that include, but are not limited to, anti-viral compounds, insecticides, fungicides, nematocides, bactericides, acaricides, growth regulators, chemosterilants, semiochemicals, repellents, attractants, pheromones, feeding stimulants, and biopesticides. Essential genes in a virus may include genes responsible for capsid production, virus assembly, infectivity, budding, and the like. The suppression of an essential gene in a virus affects the function of a gene product that enables viral infection in a plant. The compositions may include various DNA or RNA polynucleotides that modulate the expression of an essential gene in a Potexvirus.

IV. Methods for Controlling Virus Infection in Fields

An agronomic field in need of virus control may be treated by application of an agricultural chemical composition comprising the targeting polynucleotides provided herein directly to the surface of the growing plants, such as by a spray. For example, virus infection in a field of crop plants may be controlled by spraying the field with the composition. The composition can be provided as a tank mix with one or more pesticidal or herbicidal chemicals to control pests and diseases of the crop plants in need of pest and disease control, a sequential treatment of components (generally the polynucleotide containing composition followed by the pesticide), or a simultaneous treatment or mixing of one or more of the components of the composition from separate containers. Treatment of the field can occur as often as needed to provide virus control and the components of the composition can be adjusted to target specific Potexvirus species through utilization of specific polynucleotides or polynucleotide compositions capable of selectively targeting the specific virus to be controlled. The composition can be applied at effective use rates according to the time of application to the field, for example, preplant, at planting, post-planting, or post-harvest. In certain embodiments, polynucleotides of the composition can be applied at rates of at least 1 to 30 grams per acre depending on the number of targeting sequences needed for the scope of virus infection in the field.

Crop plants in which virus control may be needed include but are not limited to corn, soybean, cotton, canola, sugar beet, alfalfa, sugarcane, rice, barley, and wheat; vegetable plants including, but not limited to, tomato, sweet pepper, tobacco, hot pepper, melon, watermelon, cucumber, zucchini, eggplant, cauliflower, broccoli, lettuce, spinach, onion, peas, carrots, sweet corn, Chinese cabbage, leek, fennel, pumpkin, squash or gourd, radish, potato, Brussels sprouts, tomatillo, tobacco, peanut, garden beans, dry beans, or okra; culinary plants including, but not limited to, basil, parsley, coffee, or tea; or fruit plants including but not limited to apple, pear, cherry, peach, plum, apricot, banana, plantain, table grape, wine grape, citrus, avocado, mango, or berry; a tree grown for ornamental or commercial use, including, but not limited to, a fruit or nut tree; ornamental plant (e.g., an ornamental flowering plant or shrub or turf grass), such as iris and impatiens. The methods and compositions provided herein can also be applied to plants produced by a cutting, cloning, or grafting process (i.e., a plant not grown from a seed) including fruit trees and plants that include, but are not limited to, avocados, tomatoes, eggplant, cucumber, melons, watermelons, and grapes, as well as various ornamental plants.

The methods provided may be applied to plants that are transgenic or non-transgenic. Non-limiting examples of transgenic plants include those that comprise one or more transgene conferring a trait selected from the group consisting of insect resistance, pesticide resistance, enhanced shelf life, fruit coloring, fruit ripening, fruit sweetness, nutritional value, and the like.

V. Identification of Polynucleotide Molecules

The polynucleotide molecules provided are designed to modulate expression by inducing regulation or suppression of a viral gene and are designed to have a nucleotide sequence essentially identical or essentially complementary to the nucleotide sequence of a viral gene or to the sequence of RNA transcribed from a viral gene of a plant, the sequence thereof determined by isolating the gene or a fragment of the gene from the plant, which can be coding sequence or non-coding sequence. Effective molecules that modulate expression are referred to as "targeting polynucleotides" or "targeting sequences" or "RNAi targeting sequences." By "essentially identical" or "essentially complementary" is meant that targeting polynucleotides (or at least a portion of a polynucleotide) are designed to hybridize to the endogenous gene noncoding sequence or to RNA transcribed (known as messenger RNA or an RNA transcript) from the endogenous gene to effect regulation or suppression of expression of the endogenous gene. Targeting polynucleotide molecules are identified by "tiling" the gene targets with partially overlapping probes or non-overlapping probes of polynucleotides that are essentially identical or essentially complementary to the nucleotide sequence of a viral gene. Multiple target sequences can be aligned and sequence regions with homology in common, according to the methods, are identified as potential targeting sequences for the multiple targets. Multiple targeting molecules of various lengths, for example 18-25 nucleotides, 26-50 nucleotides, 51-100 nucleotides, 101-200 nucleotides, 201-300 nucleotides or more can be pooled into a few treatments in order to investigate polynucleotide molecules that cover a portion of a gene sequence (for example, a portion of a coding versus a portion of a noncoding region, or a 5' versus a 3' portion of a gene) or an entire gene sequence including coding and noncoding regions of a target gene. Polynucleotide molecules of the pooled targeting molecules can be divided into smaller pools or single molecules in order to identify targeting molecules that provide the desired effect.

The target gene may be sequenced by any number of available methods and equipment known in the art. Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.). In addition to the single molecule sequencing performed using sequencing-by-synthesis of Helicos Biosciences, other single molecule sequencing technologies are encompassed and include the SMRT™ technology of Pacific Biosciences, the Ion Torrent™ technology, and nanopore sequencing being developed for example, by Oxford Nanopore Technologies. A viral target gene comprising DNA or RNA can be isolated using primers or probes essentially complementary or essentially homologous to the target gene or a fragment thereof. A polymerase chain reaction (PCR) gene fragment can be produced using primers essentially complementary or essentially homologous to a viral gene or a fragment thereof that is useful to isolate a viral gene from a plant genome. Various sequence capture technologies can be used to isolate additional target gene sequences, for example, including but not limited to Roche NimbleGen® (Madison, WI) and Streptavdin-coupled Dynabeads® (Life Technologies, Grand Island, NY) and US20110015084, herein incorporated by reference in its entirety.

Embodiments of functional single-stranded or double-stranded polynucleotides have sequence complementarity that need not be 100 percent, but is at least sufficient to permit hybridization to RNA transcribed from the target gene or DNA of the target gene to form a duplex to permit a gene silencing mechanism. Thus, in embodiments, a polynucleotide fragment is designed to be complementary to all or a portion of an essential target Potexvirus gene sequence. For instance, the fragment may be essentially identical or essentially complementary to a sequence of 18 or more contiguous nucleotides in either the target viral gene sequence or messenger RNA transcribed from the target gene. In certain embodiments, a "fragment" may comprise at least 18, at least 19, at least 20, at least 25, at least 30, at least 35, at least 40, at least 45, at least 50, at least 60, at least 70, at least 80, at least 90, at least 100, at least 150, at least 200, or more contiguous nucleotides in either the target viral gene sequence or messenger RNA transcribed from the target gene. By "essentially identical" is meant having 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the target gene or RNA transcribed from the target gene; by "essentially complementary" is meant having 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene. In some embodiments, polynucleotide molecules are designed to have 100 percent sequence identity with or complementarity to one allele or one family member of a given target gene (coding or non-coding sequence of a gene); in other embodiments the polynucleotide molecules are designed to have 100 percent sequence identity with or complementarity to multiple alleles or family members of a given target gene.

"Identity" or "sequence identity" refers to the degree of similarity between two polynucleic acid or protein sequences. An alignment of the two sequences is performed by a suitable computer program. A widely used and accepted computer program for performing sequence alignments is CLUSTALW v1.6 (Thompson, et al. *Nucl. Acids Res.*, 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between a 200 and a 400 amino acid protein, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Targeting polynucleotide molecules for specific viral gene family members or broad anti-viral activity can be identified from coding and/or non-coding sequences of gene families of a plant virus or multiple plant viruses, by aligning and selecting 200-300 polynucleotide fragments from the least homologous regions among the aligned sequences and evaluated using topically applied polynucleotides (antisense ssDNA or dsRNA) to determine their relative effectiveness in providing the anti-viral phenotype. In some embodiments, the viral gene family is Flexiviridae and the sequences are selected from SEQ ID NOs:1-14 or those listed in Tables 1 and 2. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the anti-viral phenotype. Once relative effectiveness is determined, the fragments are utilized singly, or again evaluated in combination with one or more other fragments to determine the targeting sequence composition or mixture of targeting polynucleotides for providing the anti-viral phenotype.

Methods of making polynucleotides are well known in the art. Chemical synthesis, in vivo synthesis and in vitro synthesis methods and compositions are known in the art and include various viral elements, microbial cells, modified polymerases, and modified nucleotides. Commercial preparation of oligonucleotides often provides two deoxyribonucleotides on the 3' end of the sense strand. Long polynucleotide molecules can be synthesized from commercially available kits. Long polynucleotide molecules can also be assembled from multiple DNA fragments. In some embodiments design parameters such as Reynolds score (Reynolds et al. *Nature Biotechnology* 22, 326-330 (2004), Tuschl rules (Pei and Tuschl, *Nature Methods* 3(9):670-676, 2006), i-score (*Nucleic Acids Res* 35:e123, 2007), i-Score Designer tool and associated algorithms (*Nucleic Acids Res* 32:936-948, 2004. *Biochem Biophys Res Commun* 316:1050-1058, 2004, *Nucleic Acids Res* 32:893-901, 2004, *Cell Cycle* 3:790-5, 2004, *Nat Biotechnol* 23:995-1001, 2005, *Nucleic Acids Res* 35:e27, 2007, *BMC Bioinformatics* 7:520, 2006, *Nucleic Acids Res* 35:e123, 2007, *Nat Biotechnol* 22:326-330, 2004) are known in the art and may be used in selecting polynucleotide sequences effective in gene silencing. In some embodiments the sequence of a polynucleotide is screened against the genomic DNA of the intended plant to minimize unintentional silencing of other genes.

Ligands can be tethered to an ssDNA or dsRNA polynucleotide. Ligands in general can include modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids (e.g., cholesterol, a bile acid, or a fatty acid (e.g., lithocholic-oleyl, lauroyl, docosnyl, stearoyl, palmitoyl, myristoyl oleyl, linoleoyl), steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. The ligand may also be a recombinant or synthetic molecule, such as a synthetic polymer, e.g., polyethylene glycol (PEG), PEG-40K, PEG-20K and PEG-5K. Other examples of ligands include lipophilic molecules, e.g., cholesterol, cholic acid, adamantane acetic acid, 1-pyrene butyric acid, dihydrotestosterone, glycerol (e.g., esters and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., lauroyl, docosnyl, stearoyl, oleyl, linoleoyl 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dodecanoyl, lithocholyl, 5β-cholanyl, N,N-distearyl-lithocholamide, 1,2-di-O-stearoylglyceride, dimethoxytrityl, or phenoxazine) and PEG (e.g., PEG-5K, PEG-20K, PEG-40K). Preferred lipophilic moieties include lipid, cholesterols, oleyl, retinyl, or cholesteryl residues.

VI. Definitions

The following definitions and methods are provided to guide those of ordinary skill in the art. Unless otherwise noted, terms are to be understood according to conventional usage by those of ordinary skill in the relevant art. Where a term is provided in the singular, the inventors also contemplate aspects described by the plural of that term.

A "targeting polynucleotide" or "targeting sequence" or "RNAi targeting sequence" is a polynucleotide molecule that is homologous or complementary to at least a portion of a target gene. Polynucleotide molecules comprising a targeting sequence are capable of modulating expression of the target gene when topically applied to a plant surface with a transfer agent. In certain embodiments, a virus-infected plant that is treated with a polynucleotide comprising a targeting sequence is able to sustain its growth, development, or reproductive ability, or said plant is less sensitive to infection from a virus as a result of said polynucleotide relative to a plant not treated with said polynucleotide. A plant treated with a composition comprising a targeting sequence may reduce or be resistant to viral expression as a result of said composition relative to a plant not treated with a composition comprising the targeting sequence. Targeting sequences disclosed herein may be generally described in relation to the target gene sequence in an antisense (complementary) or sense orientation as ssDNA, dsDNA, ssRNA, or dsRNA molecules or nucleotide variants and modified nucleotides thereof depending on the various regions of a gene being targeted.

As used herein, the term "DNA," "DNA molecule," or "DNA polynucleotide molecule" refers to an ssDNA or dsDNA molecule of genomic or synthetic origin, such as a polymer of deoxyribonucleotide bases or a DNA polynucleotide molecule. As used herein, the term "DNA sequence," "DNA nucleotide sequence," or "DNA polynucleotide sequence" refers to the nucleotide sequence of a DNA molecule. Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, the term "RNA," "RNA molecule," or "RNA polynucleotide molecule" refers to a ssRNA or dsRNA molecule of genomic or synthetic origin, such as a polymer of ribonucleotide bases or an RNA polynucleotide molecule. As used herein, the term "RNA sequence," "RNA nucleotide sequence," or "RNA polynucleotide sequence" refers to the nucleotide sequence of an RNA molecule. Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, "polynucleotide" refers to a DNA or RNA molecule containing multiple nucleotides and generally also refers to "oligonucleotides" (a polynucleotide molecule of typically 50 or fewer nucleotides in length). Embodiments include compositions including oligonucleotides having a length of 18-25 nucleotides (18-mers, 19-mers, 20-mers, 21-mers, 22-mers, 23-mers, 24-mers, or 25-mers), for example, oligonucleotides as set forth as SEQ ID NOs:1-14, or listed in Tables 1 and 2, or fragments thereof. A target gene comprises any polynucleotide molecule in a plant cell or fragment thereof for which the modulation of the expression of the target gene is provided by the methods and compositions. A gene has noncoding genetic elements (components) that provide for the function of the gene, these elements are polynucleotides that provide gene expression regulation, such as, a promoter, an enhancer, a 5' untranslated region, intron regions, and a 3' untranslated region. Oligonucleotides and polynucleotides can be made to any of the genetic elements of a gene and to polynucleotides spanning the junction region of a genetic element, such as, an intron and exon, the junction region of a promoter and a transcribed region, the junction region of a 5' leader and a coding sequence, the junction of a 3' untranslated region and a coding sequence.

Polynucleotide compositions used in the various embodiments include compositions including oligonucleotides or polynucleotides, or a mixture of both, of DNA or RNA, or chemically modified oligonucleotides or polynucleotides or a mixture thereof. In some embodiments, the polynucleotide includes chemically modified nucleotides. Examples of chemically modified oligonucleotides or polynucleotides are well known in the art; see, for example, US Patent Publication 20110171287, US Patent Publication 20110171176, and US Patent Publication 20110152353, US Patent Publication, 20110152346, US Patent Publication 20110160082, herein incorporated in its entirety by reference hereto. For example, including, but not limited to, the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (for example, fluorescein or rhodamine) or other label (for example, biotin).

The term "gene" refers to components that comprise chromosomal DNA, RNA, plasmid DNA, cDNA, intron and exon DNA, artificial DNA polynucleotide, or other DNA that encodes a peptide, polypeptide, protein, or RNA transcript molecule, and the genetic elements flanking the coding sequence that are involved in the regulation of expression, such as, promoter regions, 5' leader regions, 3' untranslated region that may exist as native genes or transgenes in a plant genome. The gene or a fragment thereof is isolated and subjected to polynucleotide sequencing methods that determines the order of the nucleotides that comprise the gene. Any of the components of the gene are potential targets for a targeting oligonucleotide and polynucleotides.

The detailed description set-forth above is provided to aid those skilled in the art in practicing the present disclosure. However, the disclosure described and claimed herein is not to be limited in scope by the specific embodiments herein disclosed because these embodiments are intended as illustration of several embodiments of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are intended to fall within the scope of the appended claims.

EXAMPLES

The following examples are not intended to limit the scope of this application nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); ss, single stranded; ds, double stranded and the like.

Example 1. Assay for Identification of Effective Targeting Sequences

An assay for screening dsRNA targeting sequences directed against PepMV sequences was carried out using the following steps.
1) Inoculum was prepared and ground in phosphate buffer (pH 7-8) with a mortar and pestle. All mortars and pestles were kept on ice during the experiment.
2) 4 ml of inoculum was transferred by serological pipette to a smaller mortar and pestle.
3) 8 mg of dsRNA targeting polynucleotide was added to each (correspondingly marked) small mortar and pestle and briefly mixed.
4) Inoculate was rubbed on plants treated with celite or another abrasive for each treatment, including a rinsing step if necessary.
5) Plants were labeled and randomized, followed by monitoring plants for infection.

Example 2. Screening of 300 nt Sequences

Figure 2:
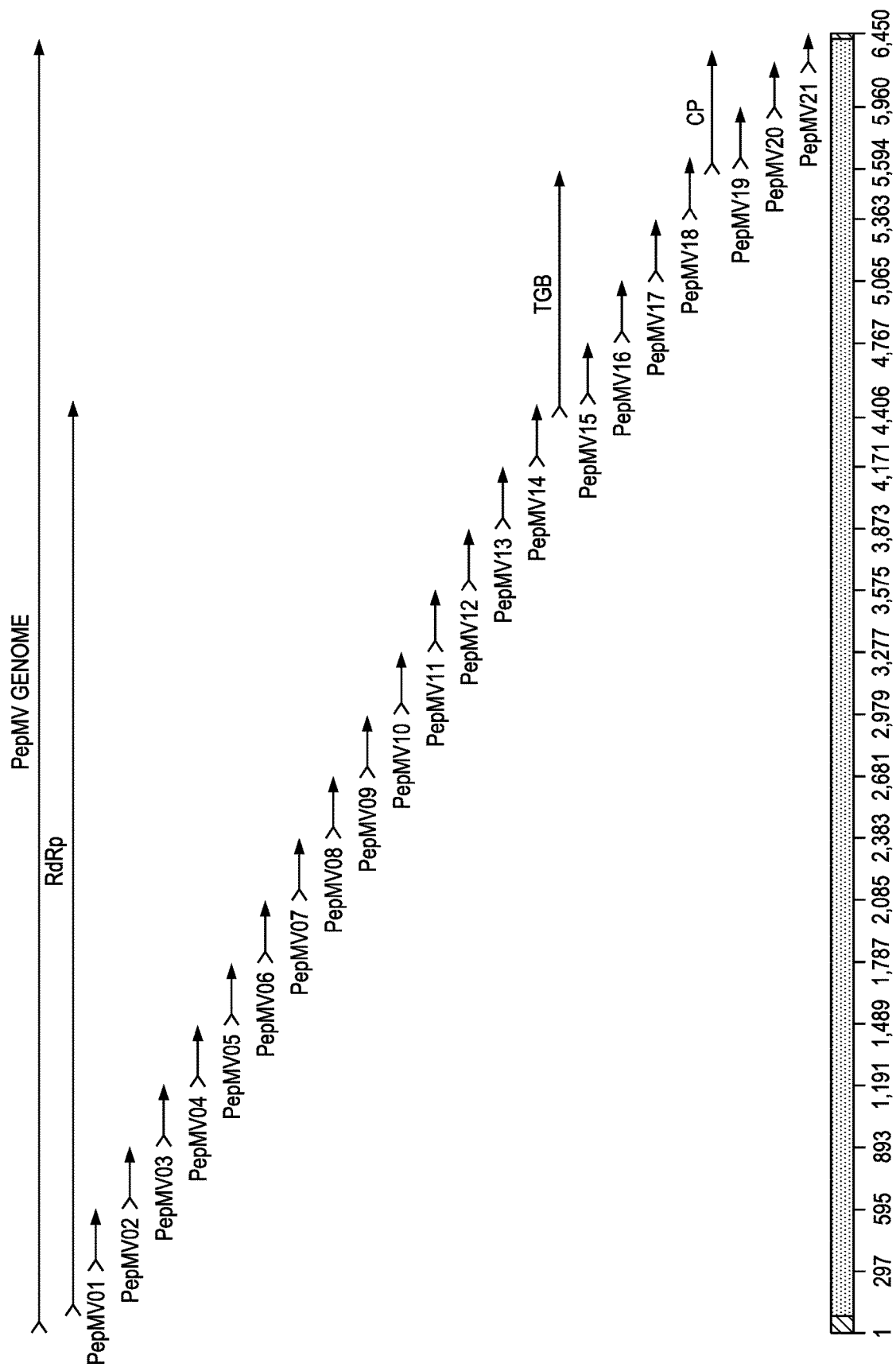
FIG. 2: Shows the design of a screen of 300 nt dsRNA targeting sequences spanning a 6450 nt region of the PepMV genome.
Figure 5:
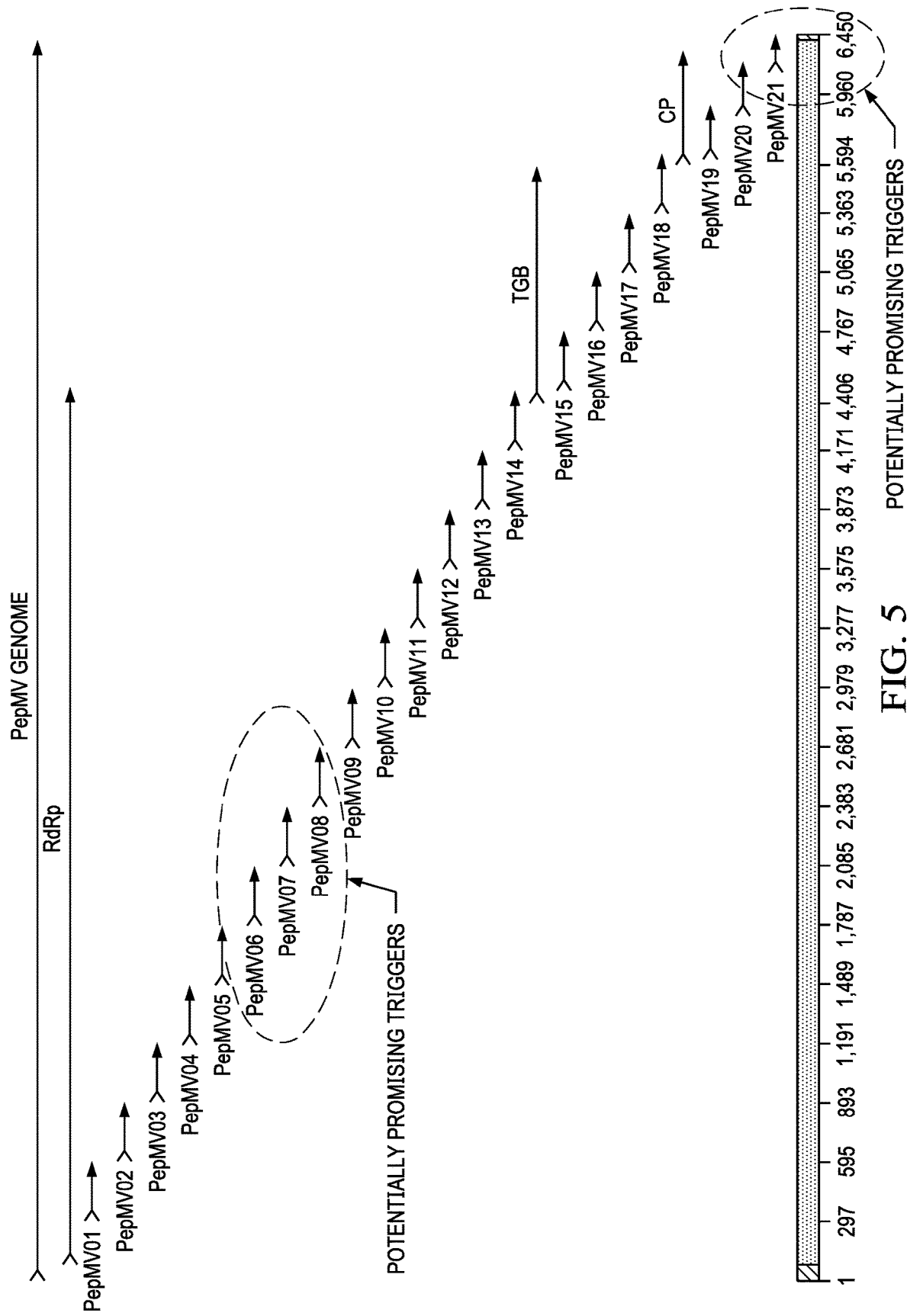
FIG. 5: Shows targeting sequences identified as being highly effective in two hotspot areas (RdRp and CP).

The first round of targeting sequence screening was designed to include 21 targeting sequences comprising 300 nt each spanning a 6450 nt region of the PepMV genome (FIG. 2). Targeting sequences were applied to plants as described above. The average disease index score was calculated for plants treated with each of the 21 targeting sequences (FIG. 3). The percentage of plants with a disease index rating of 1 (i.e., no clear signs or symptoms of infection) over the whole experiment was calculated for plants treated with each targeting sequence to identify potentially promising targeting sequences (FIG. 4). Targeting sequences designated PepMV06, PepMV07, PepMV08, and PepMV21 in two hotspot areas (RdRp and CP) were identified for further study (FIG. 5).

Example 3. Screening of Sequences in Target Areas

Figure 6:
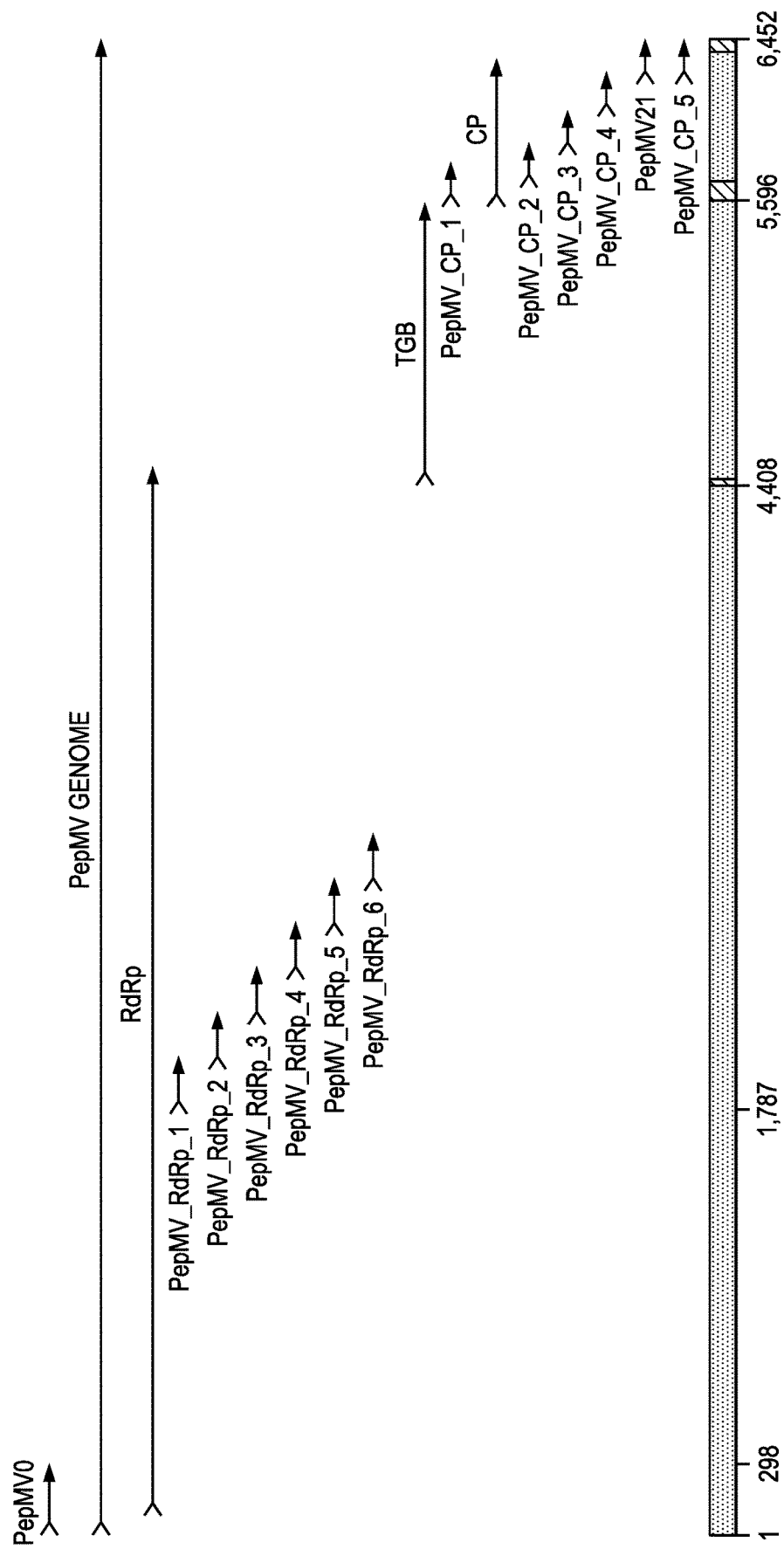
FIG. 6: Shows additional targeting sequences designed to focus on three identified target areas within the PepMV genome, including the 5' end of the genome, the RNA dependent RNA polymerase (RdRp) gene, and the capsid protein (CP) gene.

Additional targeting sequences were designed to focus on three identified target areas within the PepMV genome, including the 5' end of the genome, the RNA dependent RNA polymerase (RdRp) gene, and the capsid protein (CP) gene (FIG. 6). The 5' region was not included in previous scans, while the RdRp and CP regions were identified as promising areas. A sequence targeting the CP (PepMV21) was the most efficacious in previous replicates.

Figure 7:
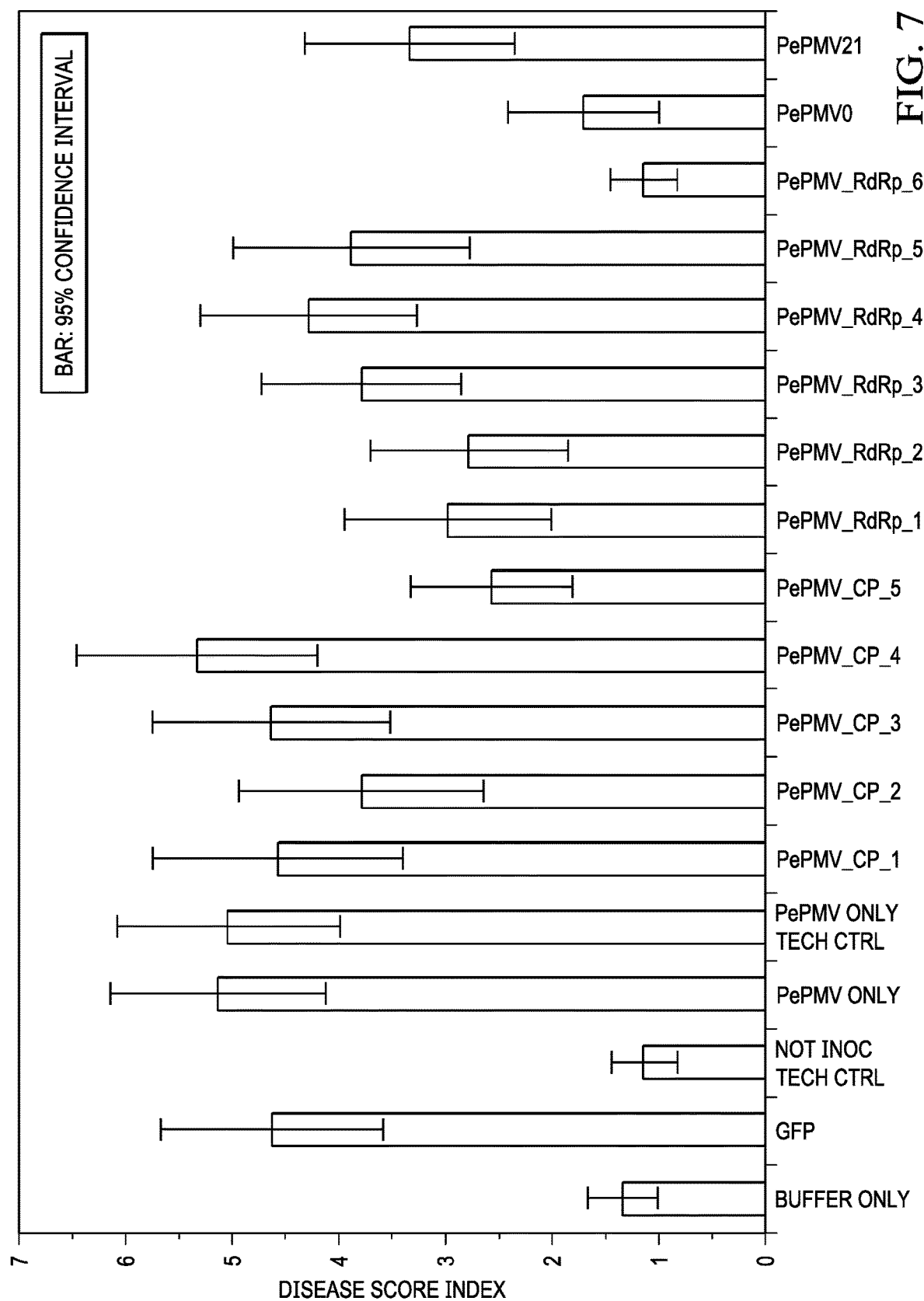
FIG. 7: Shows average DSI scores for plants treated with several dsRNA targeting sequences compared with controls.
Figure 8:
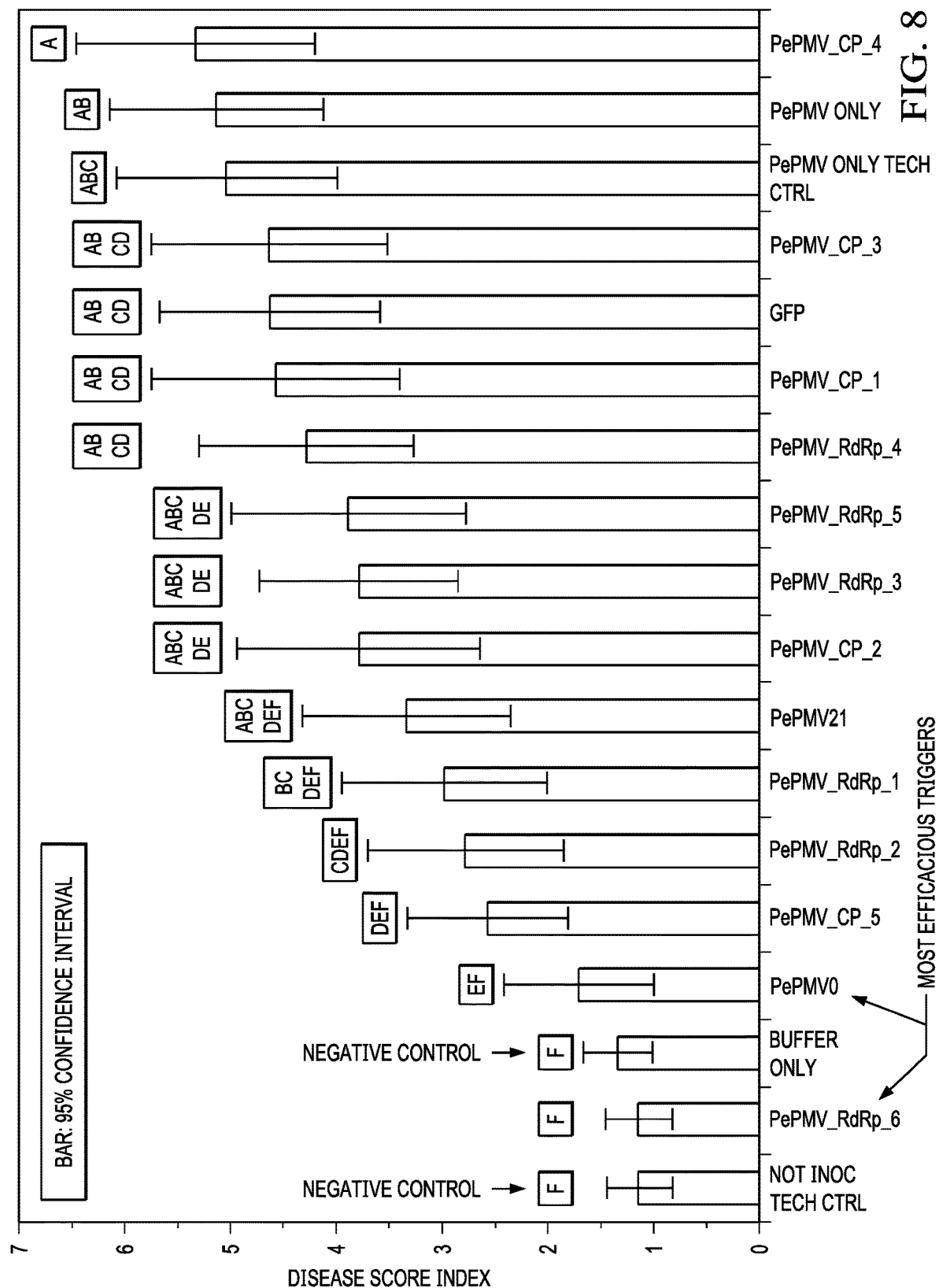
FIG. 8: Shows average DSI scores for plants treated with several dsRNA targeting sequences compared with controls.

For this screen, 14 PepMV targeting sequences were compared with 5 controls (positive, negative, GFP, buffer only, tech positive control) as shown in Table 1. Forty plants per treatment were evaluated in 4 RCB replicates. Targeting sequences were applied through a direct spike of dsRNA into inoculum at 2 mg dsRNA/ml of inoculum. Plants were inoculated by rubbing and visually assessed using DSI scores. Average DSI scores for plants treated with targeting sequences compared with controls are shown in FIG. 7 and FIG. 8.

TABLE 1

Targeting sequences for screening of target
areas of the PepMV genome.

| Description | Type | SEQ ID NO. |
|---|---|---|
| PepMV0 | dsRNA | 1 |
| GFP | dsRNA | 2 |
| PepMV_CP_1 | dsRNA | 3 |
| PepMV_CP_2 | dsRNA | 4 |
| PepMV_CP_3 | dsRNA | 5 |
| PepMV_CP_4 | dsRNA | 6 |
| PepMV_CP_5 | dsRNA | 7 |
| PepMV21 | dsRNA | 8 |
| PepMV_RdRp_1 | dsRNA | 9 |
| PepMV_RdRp_2 | dsRNA | 10 |
| PepMV_RdRp_3 | dsRNA | 11 |
| PepMV_RdRp_4 | dsRNA | 12 |
| PepMV_RdRp_5 | dsRNA | 13 |
| PepMV_RdRp_6 | dsRNA | 14 |

Figure 9:
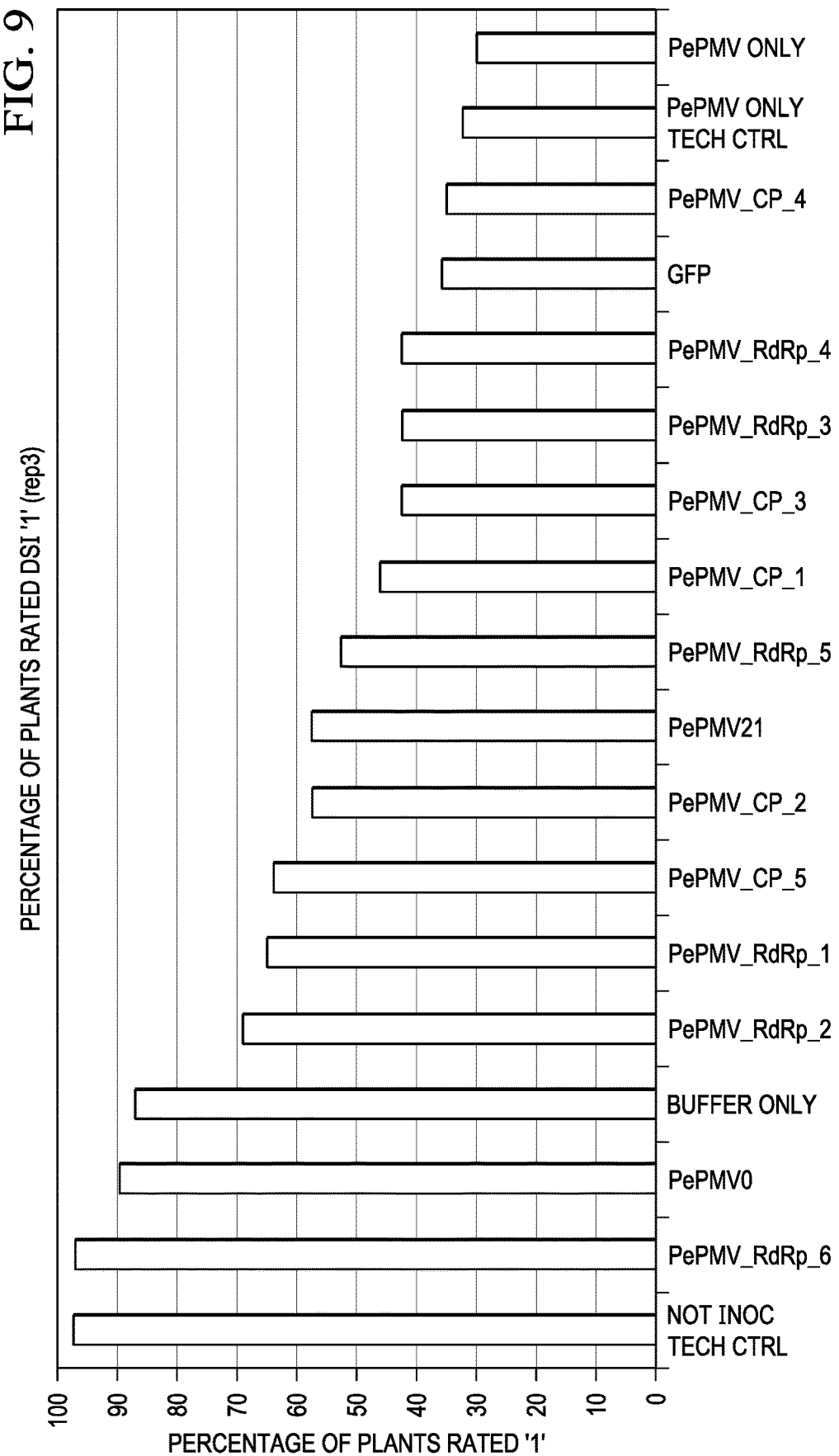
FIG. 9: Shows the percentage of plants with a DSI rating of '1' when treated with several dsRNA targeting sequences.

The percentage of plants with a DSI rating of '1' are shown in FIG. 9. In this experiment, 97% of plants treated with PepMV_RdRp_6 (SEQ ID NO: 14) were rated disease-free, compared to 35% of plants treated with a control sequence and 30% of unprotected plants challenged with PepMV. Further, 90% of plants treated with PepMV0 (SEQ ID NO: 1) and 64% of plants treated with PepMV_CP_5 (SEQ ID NO: 7) were rated with the lowest disease score rating of '1' several weeks after inoculation, appearing uninfected and without characteristic PepMV symptoms. In contrast, the majority of the plants treated with control polynucleotides displayed moderate or severe PepMV symptoms.

Figure 10:
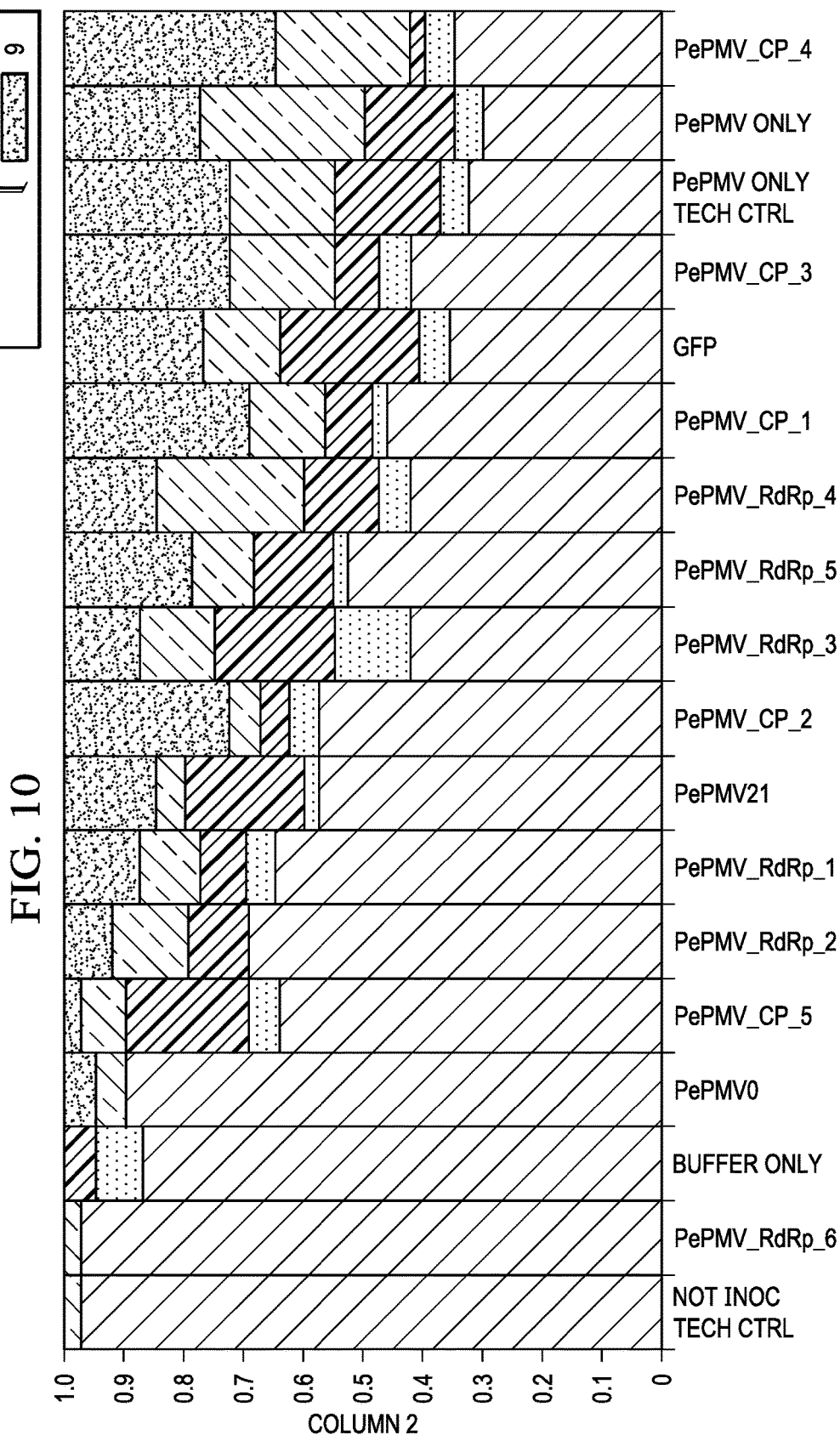
FIG. 10: Shows the proportion of plants with different DSI ratings for various targeting sequence treatments.

The proportion of plants with different DSI ratings for various targeting sequence treatments is shown in FIG. 10. Highly efficacious targeting sequences, including PepMV_RdRp_6 and PepMV0, resulted in fewer plants becoming infected and the infected plants in these treatments were generally less symptomatic.

Figure 11:
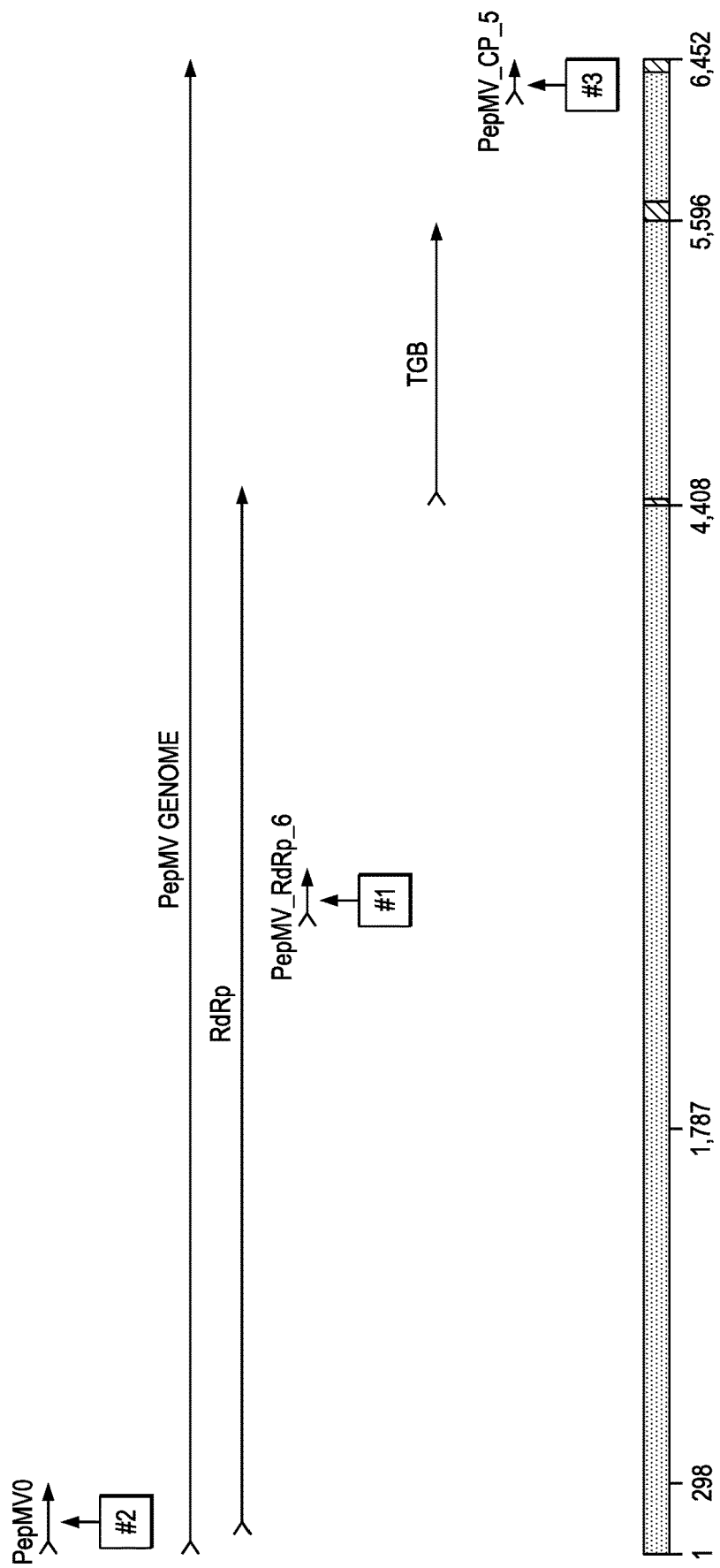
FIG. 11: Shows the location of highly efficacious targeting sequences against PepMV within the PepMV genome.

The locations of highly efficacious targeting sequences against PepMV within the PepMV genome are shown in FIG. 11.

Example 4. Further Characterization of Highly Effective Targeting Sequences

Figure 12:
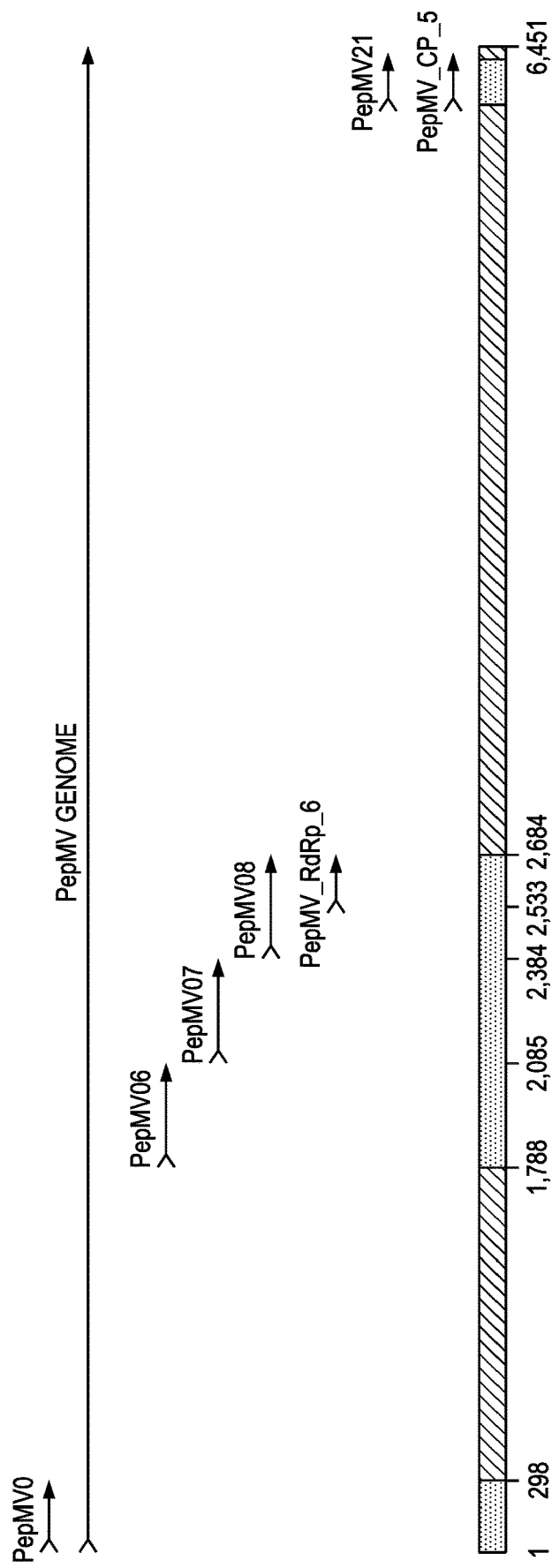
FIG. 12: Shows the location of additional highly efficacious targeting sequences within the PepMV genome.

A diagram detailing the location of identified highly efficacious targeting sequences is shown in FIG. 12, and the nucleotide binding sites within the PepMV genome are shown in Table 2. The targeting sequences were designed using the PepMV Sp-13 sequence (Genbank accession AF484251), while screening was carried out using PepMV CH2 (Genbank accession JN835466). Targeting sequences were not completely complementary to the virus strain used, and in some cases there was moderate sequence divergence as shown in Table 2.

TABLE 2

Targeting sequences and nucleotide binding
sites identified through screening.

| Targeting Sequence | Start Nucleotide | End Nucleotide | SEQ ID NO. | Efficacy | % Identity to CH2 strain |
|---|---|---|---|---|---|
| PepMV0 | 2 | 297 | 1 | High | 88 |
| PepMV06 | 1789 | 2086 | 18 | Moderate | 73 |
| PepMV07 | 2087 | 2384 | 19 | Moderate | 80 |
| PepMV08 | 2385 | 2682 | 20 | Moderate | 85 |
| PepMV_RdRp_6 | 2534 | 2684 | 14 | High | 86 |
| PepMV21 | 6258 | 6413 | 8 | High | 89 |
| PepMV_CP5 | 6262 | 6412 | 7 | High | 89 |

As shown in Table 2, the identified targeting sequences are efficacious against moderately divergent viral isolates of PepMV. There are 35 species of Potexvirus recognized by the International Committee on Taxonomy of Viruses and, besides PepMV, Potato virus X is by far the most widespread and economically significant. Table 3 shows the currently recognized members of the Potexvirus genus and their relevant Genbank accession IDs (where available).

TABLE 3

Species of Potexvirus with exemplary
accession numbers.

| Species | Exemplary Accession Number |
|---|---|
| *Allium* virus X | FJ670570 |
| *Alstroemeria* virus X | AB206396 |
| *Alternanthera* mosaic virus | AY863024 |
| Asparagus virus 3 | AB304848 |
| Bamboo mosaic virus | D26017 |
| Cactus virus X | AF308158 |
| *Cassava* common mosaic virus | U23414 |
| *Cassava* virus X | NC_034375 |
| Clover yellow mosaic virus | D29630 |
| *Cymbidium* mosaic virus | U62963 |
| Foxtail mosaic virus | M62730 |
| *Hosta* virus X | AJ620114 |
| *Hydrangea* ringspot virus | AY707100 |
| *Lagenaria* mild mosaic virus | AB546335 |
| Lettuce virus X | AM745758 |
| Lily virus X | AJ633822 |
| Malva mosaic virus | DQ660333 |
| Mint virus X | AY789138 |
| *Narcissus* mosaic virus | D13747 |
| Nerine virus X | AB219105 |
| *Opuntia* virus X | AY366209 |
| Papaya mosaic virus | D13957 |
| Pepino mosaic virus | AF484251 |
| *Phaius* virus X | AB353071 |
| *Plantago asiatica* mosaic virus | Z21647 |
| Potato *aucuba* mosaic virus | S73580 |
| Potato virus X | D00344 |
| *Schlumbergera* virus X | AY366207 |
| Strawberry mild yellow edge virus | D12517 |
| Tamus red mosaic virus | JN389521 |
| Tulip virus X | AB066288 |
| White clover mosaic virus | X06728 |
| Yam virus X | KJ711908 |
| Zygocactus virus X | AY366208 |

Example 5. Activity of Targeting Sequences in Homologous Strains

As described in the previous examples, targeting sequences were shown to be effective even when not completely complementary to the virus strain used, and therefore genome accessions most closely related to PepMV were searched for homology using the most efficacious targeting sequences as queries. Regions of homology were determined using the BLAST algorithm. First, parameters were tuned to find longer but more distant nucleotide homology. Second, translated searching (tblastx) was used to find homology at the protein level. Although the targeting sequence queries may target untranslated regions, the second method is effective due to the conservation inherent in codon wobble (in many cases, similar nucleotide triplets encode the same amino acid). The regions of homology were used to create multiple species alignments of these nucleotide regions, and consensus sequences were calculated using the EMBOSS package's CONS command, with a 'plurality' setting of 0.4 and 'identity' equal to half or greater of the number of input sequences. The consensus sequences may be used to create optimized targeting sequence designs which target multiple genome accessions. Tables 4, 5, and 6 show the position of the genomic regions targeted by PepMV_RdRp_6 (SEQ ID NO: 14), PepMV_CP_5 (SEQ ID NO: 7), and PepMV0 (SEQ ID NO: 1) sequences, respectively, within several related strains. Homology to the target region to the PepMV genomic sequence as well as to target region in the Potexvirus consensus sequence is shown.

TABLE 4

Genomic regions within Potexvirus strains targeted by PepMV_RdRp_6 (SEQ ID NO: 14).

| PepMV_RdRp_6 (SEQ ID NO: 14) Genome Accession | Start | End | vs PepMV % identity (nucleotide) | vs Consensus % identity (nucleotide) | Length of region |
|---|---|---|---|---|---|
| AB206396.1 | 3026 | 3175 | 0.633 | 0.747 | 149 |
| AB219105.1 | 2781 | 2924 | 0.578 | 0.598 | 143 |
| AB353071.1 | 2123 | 2272 | 0.667 | 0.701 | 149 |
| AB546335.1 | 91 | 219 | 0.500 | 0.713 | 128 |
| AF308158.2 | 2926 | 3021 | 0.607 | 0.81 | 95 |
| AJ620114.1 | 2731 | 2880 | 0.567 | 0.782 | 149 |
| AJ633822.2 | 2129 | 2278 | 0.589 | 0.667 | 149 |
| AM745758.1 | 3216 | 3365 | 0.644 | 0.69 | 149 |
| AY366207.2 | 2931 | 3029 | 0.609 | 0.779 | 98 |
| AY366208.1 | 2923 | 3024 | 0.533 | 0.759 | 101 |
| AY366209.1 | 2905 | 3054 | 0.567 | 0.782 | 149 |
| AY707100.1 | 2403 | 2552 | 0.556 | 0.793 | 149 |
| AY863024.1 | 2903 | 2986 | 0.631 | 0.774 | 83 |
| D00344.1 | 2605 | 2748 | 0.633 | 0.828 | 143 |
| D12517.1 | 2202 | 2351 | 0.611 | 0.655 | 149 |
| D13747.1 | 3003 | 3146 | 0.667 | 0.805 | 143 |
| D13957.1 | 2872 | 3009 | 0.622 | 0.793 | 137 |
| D26017.1 | 2327 | 2461 | 0.533 | 0.69 | 134 |
| D29630.1 | 3269 | 3406 | 0.556 | 0.759 | 137 |
| DQ660333.1 | 2884 | 3027 | 0.633 | 0.678 | 143 |
| FJ670570.2 | 3384 | 3512 | 0.522 | 0.724 | 128 |
| JN389521.1 | 2749 | 2886 | 0.533 | 0.701 | 137 |
| JN835466.1 | 2528 | 2677 | 0.856 | 0.644 | 149 |
| KJ711908.1 | 2341 | 2484 | 0.544 | 0.586 | 143 |
| M62730.1 | 2211 | 2345 | 0.589 | 0.69 | 134 |
| NC_034375.1 | 2194 | 2295 | 0.644 | 0.747 | 101 |
| S73580.1 | 3038 | 3181 | 0.622 | 0.575 | 143 |
| U23414.1 | 2588 | 2737 | 0.578 | 0.667 | 149 |
| U62963.1 | 2371 | 2520 | 0.511 | 0.598 | 149 |
| X06728.1 | 2130 | 2267 | 0.467 | 0.644 | 137 |
| Z21647.1 | 2387 | 2536 | 0.511 | 0.759 | 149 |

TABLE 5

Genomic regions within Potexvirus strains targeted by PepMV_CP_5 (SEQ ID NO: 7).

| PepMV_CP_5 (SEQ ID NO: 7) Genome Accession | Start | End | vs PepMV % identity (nucleotide) | vs Consensus % identity (nucleotide) | Length of region |
|---|---|---|---|---|---|
| JN835466.1 | 6260 | 6388 | 0.827 | 0.84 | 128 |
| D13747.1 | 6792 | 6875 | 0.653 | 0.8 | 83 |
| AM745758.1 | 7055 | 7138 | 0.640 | 0.773 | 83 |
| AB206396.1 | 6849 | 6926 | 0.627 | 0.733 | 77 |
| DQ660333.1 | 6705 | 6794 | 0.613 | 0.72 | 89 |
| U62963.1 | 6069 | 6143 | 0.613 | 0.693 | 74 |
| S73580.1 | 6901 | 6975 | 0.560 | 0.627 | 74 |

TABLE 6

Genomic regions targeted by PepMV0 (SEQ ID NO: 1).

| PepMV0 (SEQ ID NO: 1) Genome Accession | Start | End | vs PepMV % identity (nucleotide) | vs Consensus % identity (nucleotide) | Length of region |
|---|---|---|---|---|---|
| JN835466.1 | 1 | 295 | 0.895 | 0.644 | 294 |
| AM745758.1 | 113 | 251 | 0.712 | 0.69 | 138 |
| AB206396.1 | 14 | 307 | 0.671 | 0.747 | 293 |
| DQ660333.1 | 82 | 291 | 0.652 | 0.678 | 209 |
| D13747.1 | 53 | 290 | 0.638 | 0.805 | 237 |
| U62963.1 | 58 | 282 | 0.619 | 0.598 | 224 |
| S73580.1 | 79 | 292 | 0.581 | 0.575 | 213 |
| X06728.1 | 108 | 317 | 0.552 | 0.644 | 209 |
| D13957.1 | 73 | 309 | 0.538 | 0.793 | 236 |
| U23414.1 | 71 | 286 | 0.533 | 0.667 | 215 |
| Z21647.1 | 86 | 295 | 0.524 | 0.759 | 209 |
| AB219105.1 | 90 | 299 | 0.524 | 0.598 | 209 |
| AY366209.1 | 58 | 288 | 0.519 | 0.782 | 230 |
| AB066288.1 | 96 | 305 | 0.519 | 0.678 | 209 |
| FJ670570.2 | 87 | 314 | 0.510 | 0.724 | 227 |
| JN389521.1 | 82 | 291 | 0.495 | 0.701 | 209 |
| D26017.1 | 95 | 304 | 0.495 | 0.69 | 209 |
| AJ620114.1 | 103 | 312 | 0.495 | 0.782 | 209 |
| D29630.1 | 95 | 304 | 0.490 | 0.759 | 209 |
| AY863024.1 | 95 | 304 | 0.490 | 0.774 | 209 |
| AF308158.2 | 85 | 294 | 0.490 | 0.81 | 209 |
| AY707100.1 | 93 | 305 | 0.486 | 0.793 | 212 |
| D00344.1 | 85 | 294 | 0.486 | 0.828 | 209 |
| AY366207.2 | 84 | 293 | 0.486 | 0.779 | 209 |
| D12517.1 | 81 | 287 | 0.469 | 0.655 | 206 |
| KJ711908.1 | 79 | 288 | 0.462 | 0.586 | 209 |
| AB353071.1 | 68 | 277 | 0.452 | 0.701 | 209 |
| NC_034375.1 | 82 | 291 | 0.449 | 0.747 | 209 |
| M62730.1 | 87 | 287 | 0.443 | 0.69 | 200 |
| AJ633822.2 | 41 | 283 | 0.438 | 0.667 | 242 |

All of the materials and methods disclosed and claimed herein can be made and used without undue experimentation as instructed by the above disclosure. Although the materials and methods disclosed herein have been described in terms of preferred embodiments and illustrative examples, it will be apparent to those of skill in the art that variations can be applied to the materials and methods described herein without departing from the concept, spirit and scope of the claims. All such similar substitutes and modifications apparent to those skilled in the art are deemed to be within the spirit, scope and concept as defined by the appended claims.

What is claimed is:

1. A method of treatment or prevention of a Pepino Mosaic Virus (PepMV) infection in a plant, the method comprising topically applying to said plant a composition comprising a double-stranded RNA polynucleotide and a transfer agent, wherein the double-stranded RNA polynucleotide consists of a first polynucleotide sequence that consists of at least 21 contiguous nucleotides of SEQ ID NO: 14 and a second polynucleotide sequence that is completely complementary to the first polynucleotide sequence, and wherein the symptoms of viral infection or development of symptoms are reduced or eliminated in said plant relative to a plant not treated with said composition when grown under the same conditions.

2. The method of claim 1, wherein said transfer agent is an organosilicone surfactant composition or compound contained therein.

3. The method of claim 2, wherein said double-stranded RNA polynucleotide consists of the nucleotide sequence of SEQ ID NO:14.

4. The method of claim 1, wherein said composition is topically applied by spraying, dusting, or is applied to the plant surface as matrix-encapsulated RNA.

5. A composition comprising a double-stranded RNA polynucleotide and a transfer agent, wherein said double-stranded RNA polynucleotide consists of a first polynucleotide sequence that consists of at least 21 contiguous nucleotides of SEQ ID NO: 14 and a second polynucleotide sequence that is completely complementary to the first polynucleotide sequence, and wherein topical application of the composition to a plant reduces or eliminates the symptoms of PepMV infection or development in said plant relative to a plant not treated with said composition when grown under the same conditions.

6. The composition of claim 5, wherein said transfer agent is an organosilicone composition.

7. The composition of claim 5, wherein said double-stranded RNA polynucleotide consists of the nucleotide sequence of SEQ ID NO:14.

8. A method of reducing expression of an essential PepMV gene comprising contacting a PepMV particle with the composition of claim 5.

9. The method of claim 8, wherein said transfer agent is an organosilicone compound.

10. The method of claim 8, wherein said double-stranded RNA polynucleotide consists of the nucleotide sequence of SEQ ID NO:14.

11. An agricultural chemical composition comprising an admixture of the composition of claim 5 and a pesticide.

12. The agricultural chemical composition of claim 11, wherein said pesticide is selected from the group consisting of anti-viral compounds, insecticides, fungicides, nematocides, bactericides, acaricides, growth regulators, chemosterilants, semiochemicals, repellents, attractants, pheromones, feeding stimulants, and biopesticides.

* * * * *